United States Patent

Failli et al.

[11] Patent Number: 5,218,124
[45] Date of Patent: Jun. 8, 1993

[54] SUBSTITUTED BENZOYLBENZENE-, BIPHENYL-AND 2-OXAZOLE-ALKANOIC ACID DERIVATIVES AS INHIBITORS OF PLA2 AND LIPOXYGENASE

[75] Inventors: Amedeo A. Failli, Princeton Junction, N.J.; Anthony F. Kreft III,, Langhorne, Pa.; John H. Musser, Alameda, Calif.; Annette L. Banker, Plainsboro, N.J.; James A. Nelson, Washington Crossing, Pa.; Uresh S. Shah, Plainsboro, N.J.; Dennis M. Kubrak, Philadelphia, Pa.

[73] Assignee: American Home Products Corporation, New York, N.Y.

[21] Appl. No.: 891,537

[22] Filed: Jun. 1, 1992

Related U.S. Application Data

[63] Continuation-in-part of Ser. No. 661,733, Feb. 27, 1991, abandoned, which is a continuation-in-part of Ser. No. 427,677, Oct. 27, 1989, abandoned.

[51] Int. Cl.$^5$ .................................. C07D 277/64
[52] U.S. Cl. .................................. 548/180; 514/365; 514/367; 514/374; 514/375; 544/283; 544/284; 544/333; 544/335; 544/336; 544/353; 544/405; 546/270; 546/271; 546/275; 546/276; 546/280; 548/204; 548/217; 548/236; 548/310.1; 548/341.1; 548/550; 548/551; 548/342.5; 549/59; 549/60; 549/452; 549/454; 562/460
[58] Field of Search ................ 548/180, 204, 217, 236

[56] References Cited

U.S. PATENT DOCUMENTS

| | | | |
|---|---|---|---|
| 3,641,127 | 2/1972 | Farge et al. | |
| 3,969,402 | 7/1976 | Adams et al. | |
| 4,659,728 | 4/1987 | Lewis et al. | 548/236 |
| 4,754,043 | 6/1988 | Kreft et al. | 548/179 |
| 4,826,990 | 5/1989 | Musser et al. | 548/203 |
| 4,895,953 | 1/1990 | Musser et al. | 548/204 |
| 5,071,988 | 10/1991 | Failli et al. | 546/174 |
| 5,084,575 | 1/1992 | Kreft et al. | 548/204 |
| 5,145,860 | 9/1992 | Takasugi et al. | 548/204 |

*Primary Examiner*—Donald G. Daus
*Attorney, Agent, or Firm*—George Tarnowski

[57] ABSTRACT

There are disclosed compounds of the formula $$A(CH_2)_nO-B$$

wherein
A is a group having the formula

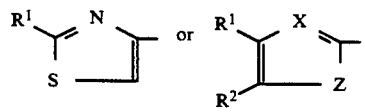

wherein
X is —N— or $$\begin{array}{c} R^3 \\ | \\ -C- \end{array};$$

Z is $$\begin{array}{cccc} R^3 \; R^3 & R^3 & & R^3 \\ | \; \; | & | & & | \\ -C=C-, & -C=N-, & -N=C-, \end{array}$$

$$\begin{array}{c} R^3 \\ | \\ -N-, \; -S- \; \text{or} \; -O-; \end{array}$$

$R^1$ is hydrogen, lower alkyl or phenyl;
$R^2$ is hydrogen or lower alkyl; or
$R^1$ and $R^2$ taken together form a benzene ring, with the proviso that when X is —N—, Z is other than $$\begin{array}{cc} R^3 \; R^3 \\ | \; \; | \\ -C=C \end{array};$$

$R^3$ is hydrogen or lower alkyl;
n is 1–2;
B is (Abstract continued on next page.)

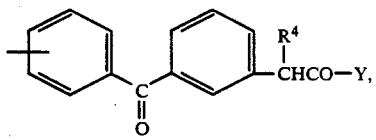

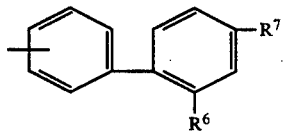

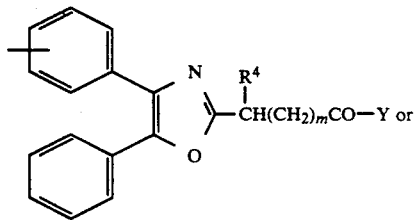

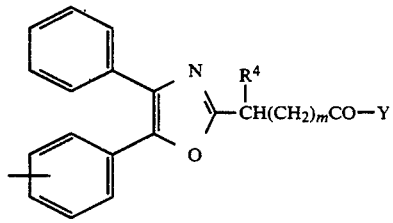

wherein

Y is $OR^5$ or $N(OH)R^8$;
$R^4$ and $R^5$ are each, independently, hydrogen or lower alkyl;
$R^6$ is hydrogen, halo or nitro;
$R^7$ is

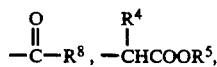

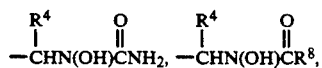

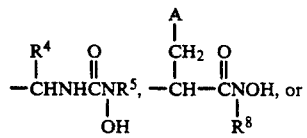

$R^8$ is lower alkyl;
m is 0–3;

and the pharmacologically acceptable salts thereof, and their use in the treatment of inflammatory conditions, such as rheumatoid arthritis, ulcerative colitis, psoriasis and other immediate hypersensitivity reactions; in the treatment of leukotriene-mediated naso-bronchial obstructive air-passageway conditions, such as allergic rhinitis, allergic bronchial asthma and the like; and as gastric cytoprotective agents.

29 Claims, No Drawings

SUBSTITUTED BENZOYLBENZENE-, BIPHENYL-AND 2-OXAZOLE-ALKANOIC ACID DERIVATIVES AS INHIBITORS OF PLA2 AND LIPOXYGENASE

This is a continuation-in-part of U.S. Ser. No. 07/661,733, filed Feb. 27, 1991 now abandoned, which is a continuation-in-part of U.S. Ser. No. 07/427,677, filed Oct. 27, 1989, now abandoned.

This invention relates to novel substituted benzoylbenzene-, biphenyl-and 2-oxazole- alkanoic acid derivatives possessing lipoxygenase inhibitory, phospholipase $A_2$ inhibitory and leukotriene antagonist activity, which are useful as anti-inflammatory, antiallergic and cytoprotective agents.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, CRC Crit. Rev. Biochem., 7, 291 (1980) and J. B. Smith, Am. J. Pathol., 99, 743 (1980). Cyclooxygenase metabolites are known to participate directly in the inflammatory response [see Higgs et al., Annals of Clinical Research, 16, 287–299 (1984)]. This is through their vasodepressor activities, participation in pain and fever augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., J. Immun., 215, 115–118 (1980); Biochem. Biophys. Res. Commun., 93, 1121–1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., Nature, 288, 484–486 (1980) and Piper, Int. Arch. Appl. Immunol., 76, suppl. 1, 43 (1985)] which stimulate the release of mucus from airways in vitro [Marom et al., Am. Rev. Resp. Dis., 126, 449 (1982)], are potent vasodilators in skin [see Bisgaard et al., Prostaglandins, 23, 797 (1982)], and produce a wheal and flare response [Camp et al., Br. J. Pharmacol., 80, 497 (1983)]. The nonpeptide leukotriene, $LTB_4$, is a powerful chemotactic factor for leukocytes [see A. W. Ford-Hutchinson, J. Roy. Soc. Med., 74, 831–833 (1981), which stimulates cell accumulation and affects vascular smooth muscle [see Bray, Br. Med. Bull., 39, 249 (1983)]. The activity of leukotrienes as mediators of inflammation and hypersensitivity is extensively reviewed in Bailey and Casey, Ann. Reports Med. Chem., 19, 87 (1986).

Phospholipase $A_2$ ($PLA_2$) is the critical rate limiting enzyme in the arachidonic acid (AA) cascade since it is responsible for the hydrolysis of esterified AA from the C-2 position of membrane phospholipids. This reaction generates two products (1) free AA which is then available for subsequent metabolism by either the cyclooxygenase or lipoxygenase enzymes and (2) lysophospholipid. When alkylarachidonoyl-glycerophosphatidylcholine is acted upon by the $PLA_2$ the generation of platelet activating factor (PAF) is initiated; PAF is pro-inflammatory in its own right [see Wedmore et al., Br. J. Pharmacol., 74, 916–917 (1981)]. In this regard it may be noted that the anti-inflammatory steroids are thought to inhibit eicosanoid synthesis by inducing the synthesis of a $PLA_2$ inhibitory protein denominated macrocortin or lipomodulin [see Flower et al., Nature, London, 278, 456 (1979) and Hirata et al., Proc. Natn. Acad. Sci. U.S.A., 77, 2533 (1980)].

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the eicosanoids and/or PAF. Thus, while $PLA_2$ has been shown to be required for platelet aggregation [Pickett et al., Biochem. J., 160, 405 (1976)], cardiac contraction and excitation [Geisler et al., Pharm. Res. Commun., 9, 117 (1977)], as well as prostaglandin synthesis [Vogt, Adv. Prostagl. Thromb. Res., 3, 89 (1978)], the inhibition of $PLA_2$ is indicated in the therapeutic treatment of both PAF induced or cyclooxygenase and/or lipoxygenase pathway product-mediated physiological conditions.

There is also evidence that products of the cyclooxygenase/lipoxygenase pathways play key roles in both the pathogenesis of gastric mucosal damage due to extracellular (gastric and intestinal contents, microorganisms, and the like) or intracellular (ischemia, viruses, etc.) agents, as well as in cytoprotection against such damage. Thus, on the one hand prostaglandins exert a cytoprotective effect on the gastric mucosa [see Robert, Gastroenterology, 77, 761–767 (1979)] and this action of the prostaglandins, especially of the E series, is considered to be of importance in the treatment of gastrointestinal ulceration [see Isselbacher, Drugs, 33 (suppl.), 38–46 (1987)]. On the other hand, ex vivo experiments have shown that gastric mucosal tissue from ethanol-pretreated rats is capable of $LTC_4$ generation and that this $LTC_4$ production is quantitatively related to the severity of the ethanol damage [see Lange et al., Naunyn-Schmiedeberg's Arch. Pharmacol. Suppl., 330, R27, (1985)]. It has also been demonstrated that $LTC_4$ can induce vasoconstriction in both venous and arteriolar vessels in the rat submucosa [see Whittle, *IUPHAR Ninth Int. Cong. of Pharm.*, S30-2, London, England (1984)]. This is significant since ethanol-induced lesion formation in gastric mucosa may be multifactorial with, for example, stasis of gastric blood flow contributing significantly to the development of the hemorrhagic necrotic aspects of the tissue injury [see Guth et al., *Gastroenterology*, 87, 1083-90 (1984)]. Moreover, in the anesthetized cat, exogenous LTD$_4$ evokes both increased pepsin secretion and decreased transgastric potential [Pendleton et al., *Eur. J. Pharmacol.*, 125, 297-99 (1986)]. A particularly significant recent finding in this regard is that 5-lipoxygenase inhibitors and some leukotriene antagonists protect the gastric mucosa against lesions induced by the oral or parenteral administration of most nonsteroidal anti-inflammatory drugs [see Rainsford, *Agents and Actions*, 21, 316-319 (1987)]. Platelet activating factor (PAF) is also implicated as a mediator of gastrointestinal damage, and it has been recently shown that 5-lipoxygenase inhibitors inhibit PAF-induced gastric mucosal damage (*Gastroenterology*, 96, A55, A434, 1989). Accordingly, a significant body of evidence implicates the involvement of lipoxygenase products in the development of pathological features associated with gastric mucosal lesions, such as for example, those induced by ethanol exposure and administration of non-steroidal anti-inflammatory drugs. Thus, compounds which inhibit the biological effects of leukotrienes and PAF and/or which control the biosynthesis of these substances, as by inhibiting 5-lipoxygenase, are considered to be of value as cytoprotective agents.

Accordingly, the biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation and for gastric cytoprotection must focus on either blocking the release of mediators of these conditions or antagonizing their effects. Thus, compounds which inhibit the biological effects of the leukotrienes and SRS's and/or which control the biosynthesis of these substances, as by inhibiting the PLA$_2$-mediated release of arachidonic acid from membrane phospholipids, or by inhibiting lipoxygenase, are considered to be of value in treating such conditions as allergic bronchial asthma, allergic rhinitis, as well as in other immediate hypersensitivity reactions and in providing gastric cytoprotection.

It has now been found that certain novel substituted benzoylbenzene-, biphenyl- and 2-oxazole- alkanoic acid derivatives inhibit PLA$_2$ and lipoxygenase, and antagonize products of the lipoxygenase pathway, and so are useful as anti-inflammatory, anti-allergic and cytoprotective agents. The present invention provides novel compounds having the following formula:

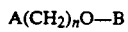

wherein
A is a group having the formula

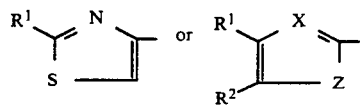

wherein

X is —N— or

Z is

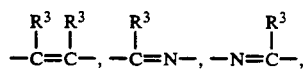

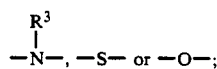

R$^1$ is hydrogen, lower alkyl or phenyl;
R$^2$ is hydrogen or lower alkyl; or
R$^1$ and R$^2$ taken together form a benzene ring, with the proviso that when X is —N—, Z is other than

R$^3$ is hydrogen or lower alkyl;
n is 1–2;
B is

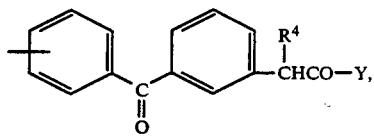

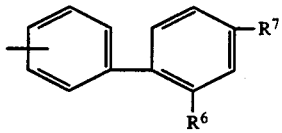

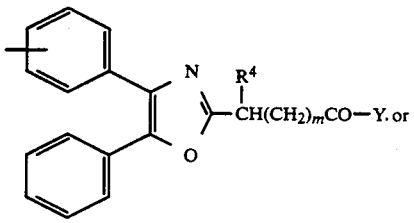

-continued

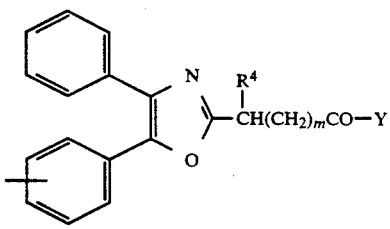

wherein

Y is $OR^5$ or $N(OH)R^8$;

$R^4$ and $R^5$ are each, independently, hydrogen or lower alkyl;

$R^6$ is hydrogen, halo or nitro;

$R^7$ is

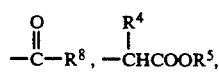

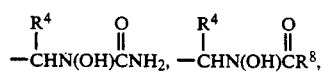

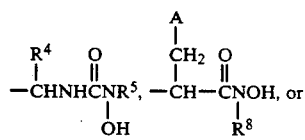

$R^8$ is lower alkyl;

m is 0–3;

and the pharmacologically acceptable salts thereof.

The term "lower alkyl" refers to moieties having 1–6 carbon atoms in the carbon chain. The term "halo" refers to fluoro, chloro or bromo.

The grouping A embraces, inter alia, 5- or 6-membered unsaturated nitrogen, sulfur or oxygen containing mono- or benzofused-heterocycles, optionally substituted with lower alkyl or phenyl. The foregoing definition embraces the following heterocyclic moieties: furyl, pyrrolyl, thienyl, oxazolyl, thiazolyl, imidazolyl, pyridyl, pyrazinyl, pyrimidinyl, benzofuranyl, benzothienyl, benzothiazolyl, indolyl, benzoxazolyl, quinazolinyl, benzimidazolyl, quinoxalinyl, quinazolinyl and the like. Especially preferred are thiazolyl, benzothiazolyl, benzoxazolyl and benzimidazolyl.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic. The compounds which are carboxylic acids are capable of forming alkali metal and alkaline earth carboxylates and carboxylates of pharmacologically acceptable cations derived from ammonia or a basic amine. Examples of the latter include but are not limited to cations such as ammonium, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The compounds of the invention can be prepared by the following reaction schemes. When it is desired to prepare compounds having the formula

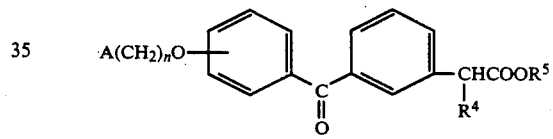

4-methoxybenzonitrile, for example, is reacted with 3-bromotoluene, followed by reaction with bromine in ethylene bromide to yield the intermediate 3-bromomethyl-[4'-methoxy]benzophenone.

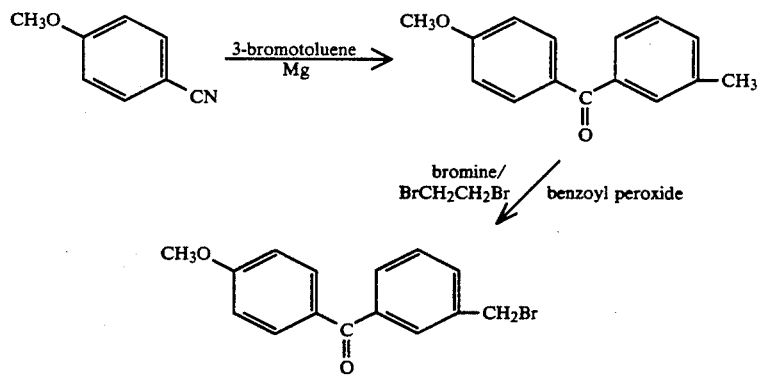

The bromo intermediate is reacted with sodium cyanide to yield the cyano intermediate, which is hydrolyzed in the presence of base to yield the carboxylic acid, which in turn is demethylated to yield the hydroxy carboxylic acid intermediate:

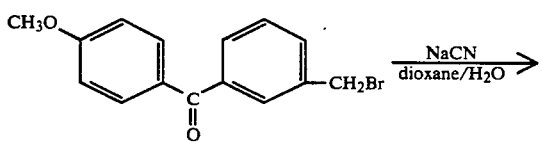

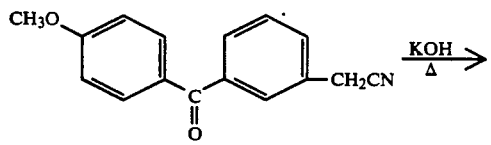

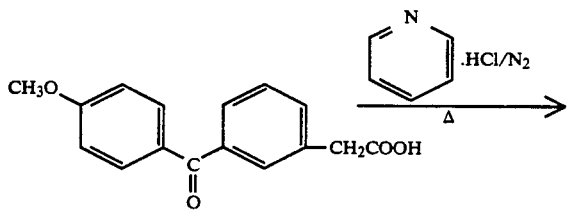

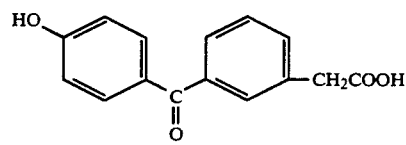

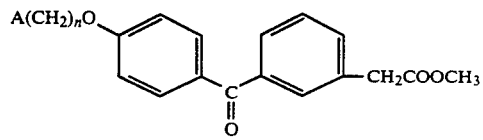

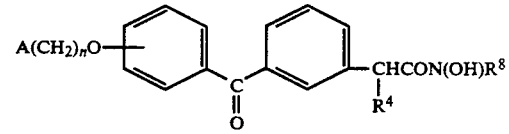

The ester can be hydrolyzed by conventional methods to yield the desired final product in free carboxylic acid form.

Compounds having the formula

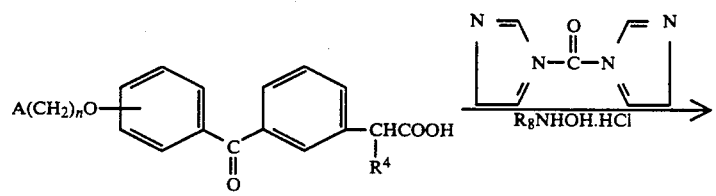

can be prepared by reacting the free carboxylic acid, whose preparation has been described above, with an appropriate N-alkylhydroxylamine in the presence of carbonyldiimidazole

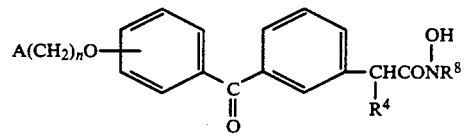

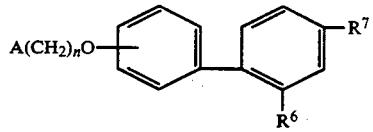

Compounds of the invention having the formula

The hydroxy carboxylic acid intermediate is converted to the methyl ester with methanol in the presence of p-toluenesulfonic acid followed by reaction with an appropriate haloalkyl-A compound, where A is as defined hereinbefore and hal is halo, to yield the desired final product as the methyl ester.

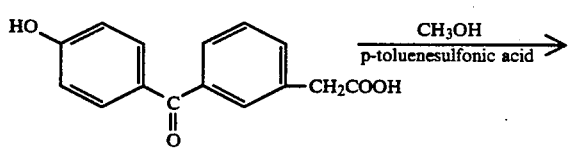

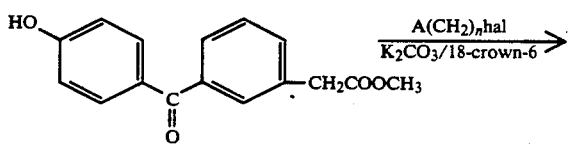

can be prepared by several routes. Compounds in which $R^6$ is nitro and $R^7$ is the $$-\overset{\overset{O}{\|}}{C}-R^8$$

moiety can be prepared as follows; for example: 4-bromo-3-nitroacetophenone is reacted with 4-iodoanisole in the presence of copper bronze, to yield the intermediate methoxy-containing biphenyl, which is demethylated with aluminum bromide to yield the hydroxy intermediate. The latter is then reacted with an appropriate haloalkyl-A compound, where A is as defined hereinbefore and hal is halo, to yield the desired final product.

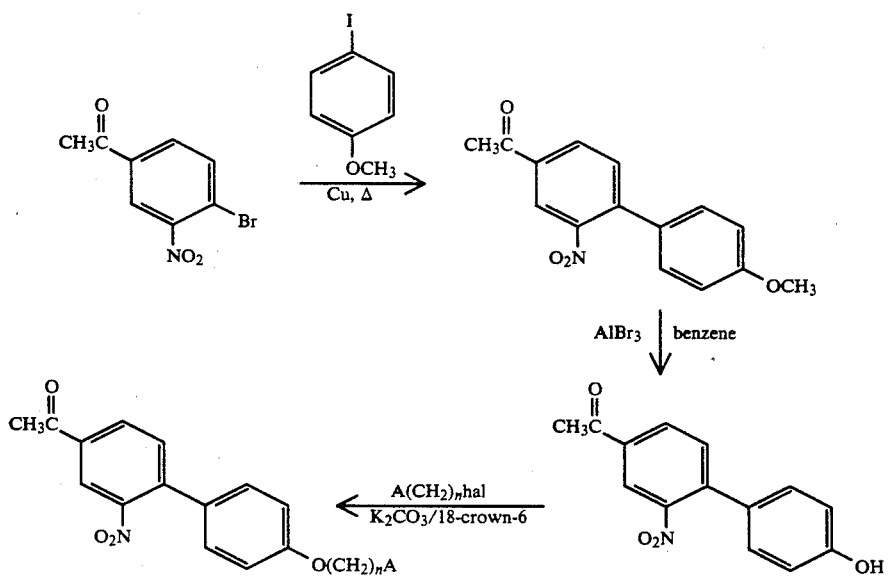

Compounds in which $R^6$ is halo and $R^7$ is the —CH$COOR^5$ moiety can be prepared by a process which utilizes the 4-methoxy-biphenyl intermediate of the preceding scheme. Thus, the 4-acetyl-4-methoxy-2-nitrobiphenyl intermediate of the previous scheme is subjected to reduction with stannous chloride to yield the intermediate amino derivative, which is then subjected to replacement of the amino group with a halo group. For example, the amino group can be replaced with fluorine via a diazonium fluoroborate transitory intermediate prepared from the amino intermediate using sodium nitrite and tetrafluoroboric acid. The resulting acetyl-fluoro-methoxy biphenyl intermediate is converted to the corresponding carboxylic acid followed by demethylation with hydrogen bromide to yield the 2-fluoro-4'-hydroxy-[1,1'-biphenyl]-4-acetic acid intermediate:

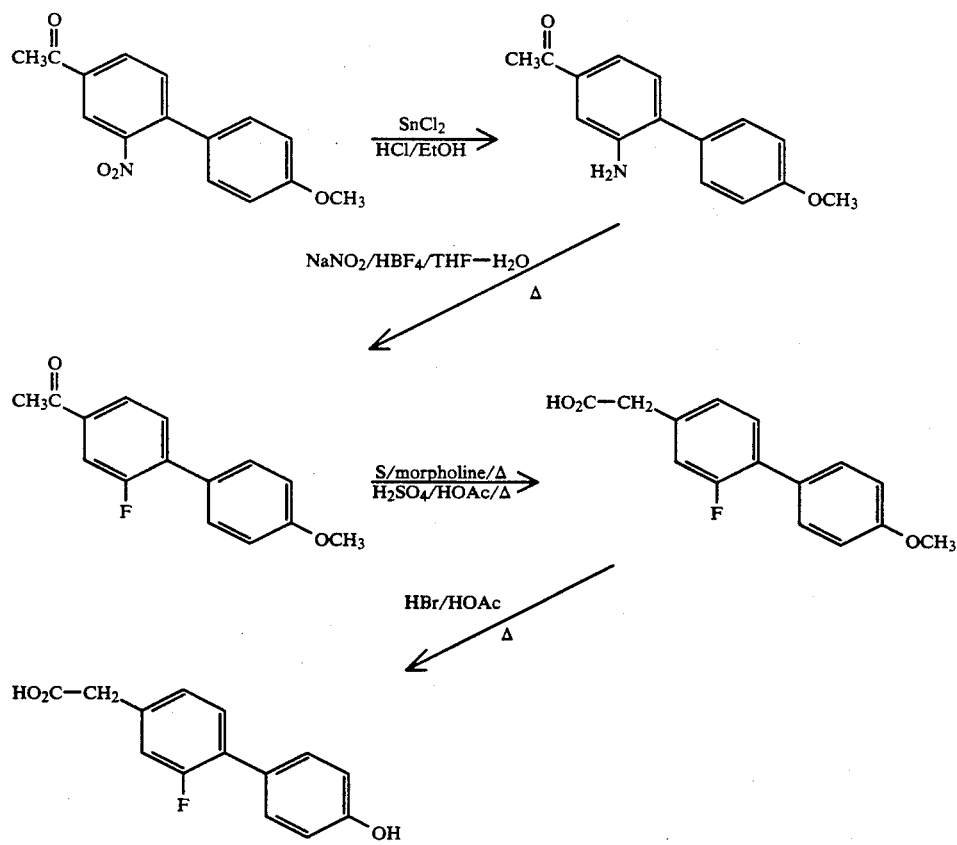

The latter carboxylic acid intermediate is esterified with methanol in the presence of p-toluenesulfonic acid and the latter is reacted with an appropriate haloalkyl-A compound, where A is as defined hereinbefore and hal is halo, to yield the desired final product as the methyl ester.

Compounds in which $R^7$ is one of the nitrogen-containing moieties can be prepared from the carboxylic acid form of the above-discussed final products. Several possible sequences for these preparations are outlined

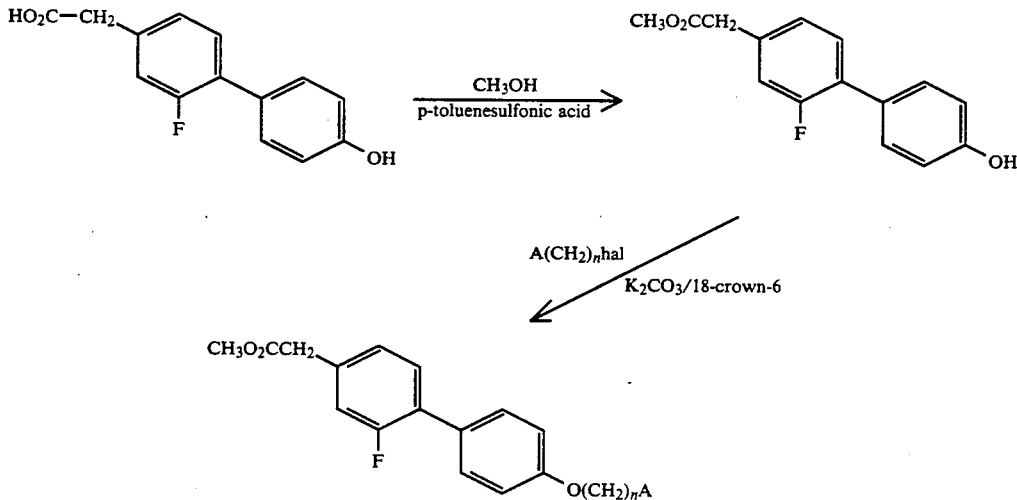

The ester can be hydrolyzed by conventional methods below:

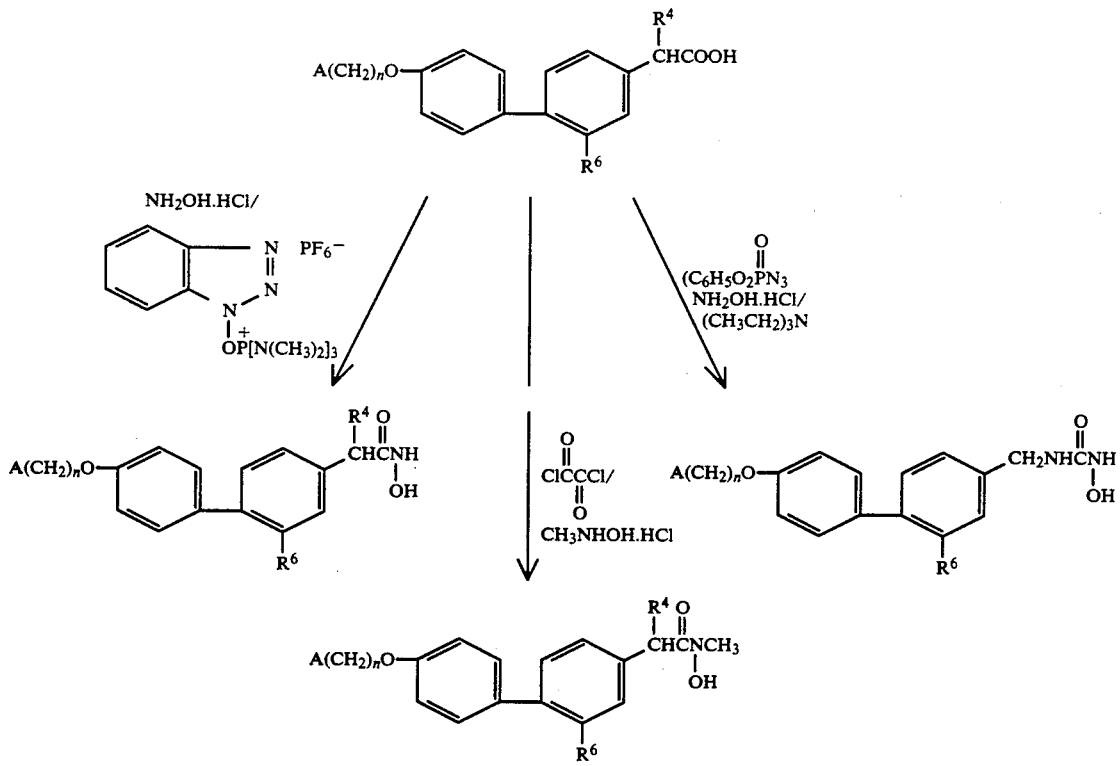

to yield the desired final product in its free carboxylic acid form.

Compounds in which $R^7$ represents a reverse hydroxamic acid or urea can be prepared according to the following scheme

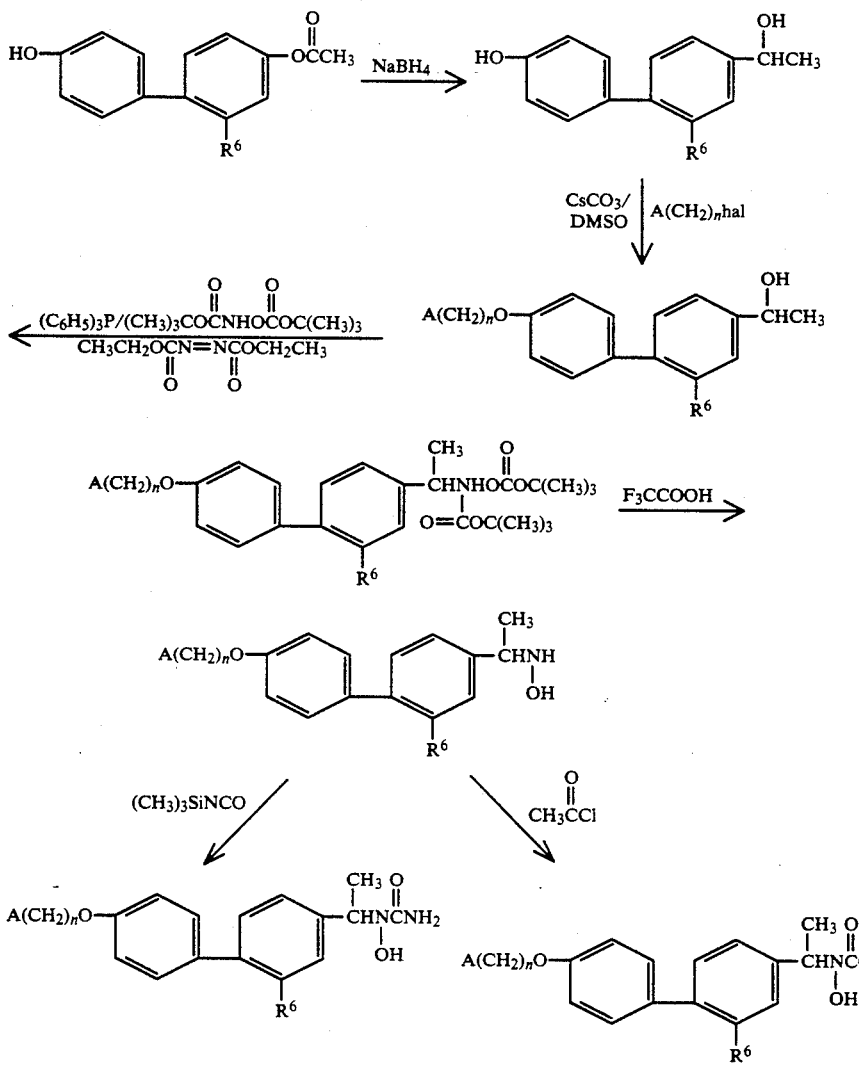
Compounds of the invention having the formula
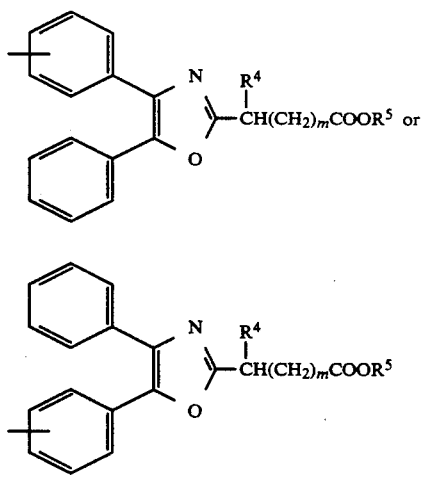
can be prepared as follows. Benzaldehyde and 4-methoxybenzaldehyde are reacted to yield 4-methoxybenzoin, which is converted to the hemisuccinate by reaction with succinic anhydride. The latter is reacted with urea and acetic acid to yield the intermediate 4-(4-methoxyphenyl)-5-phenyl-2-oxazole-propionic acid.
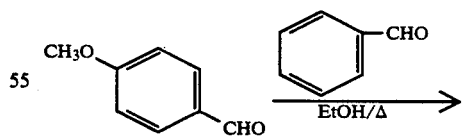
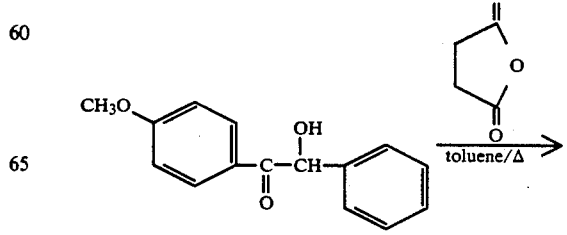

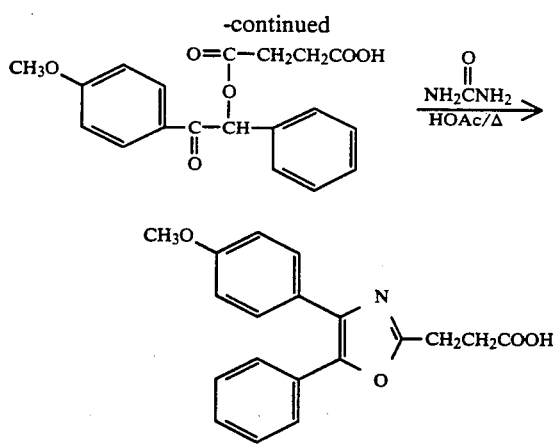

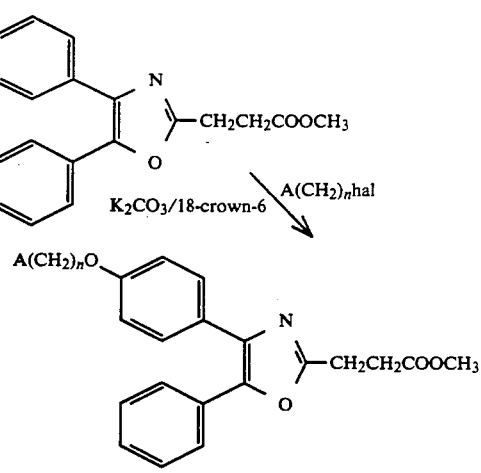

The latter intermediate is demethylated with hydrogen bromide and esterified with methanol to yield the corresponding hydroxy methyl ester intermediate, which is then reacted with an appropriate haloalkyl-A compound, where A is as defined hereinbefore and hal is halo, to yield the desired final product as the methyl ester.

The ester can be hydrolyzed by conventional methods to yield the desired final product in its free carboxylic acid form.

Compounds of the invention having the formula

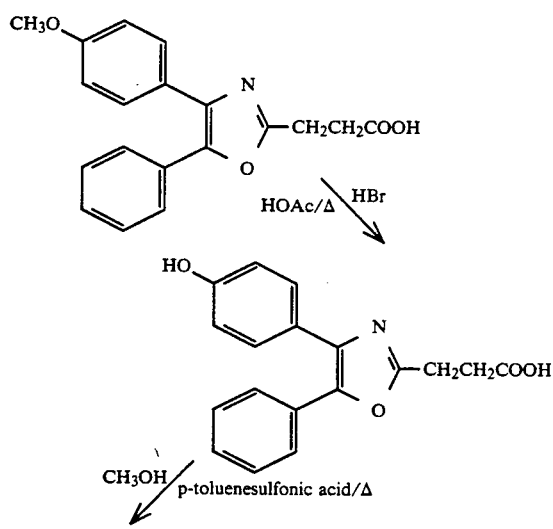

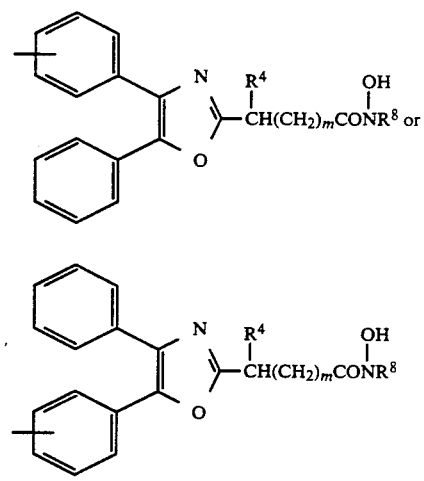

can be prepared from the carboxylic acid form of the above-discussed final products. Thus, the free acid is reacted with an appropriate N-alkylhydroxylamine in the presence of carbonyldiimidazole:

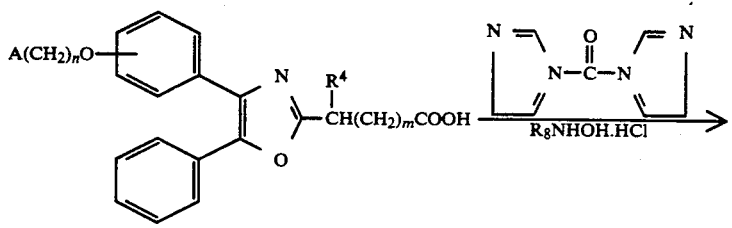

-continued

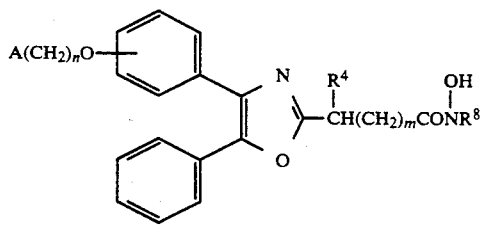

The conventional starting materials used in the reaction sequences outlined above are available commercially or can be prepared by methods known in the art. Thus, for example, the intermediate compound 2-bromomethylquinoline can be prepared by the following reaction sequence:

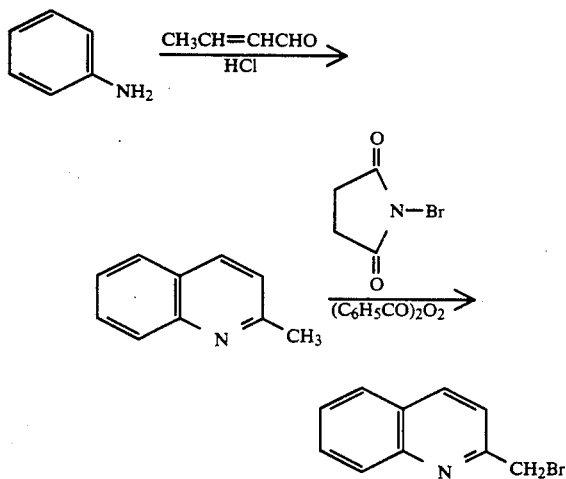

The benzo-fused heterocyclic compounds used in the above reaction sequences are also either commercially available or can be prepared by methods conventional in the art. Thus, for example, such intermediates as 1-methyl-2-chloromethylbenzimidazole, 2-chloromethylbenzthiazole and 2-chloromethylbenzoxazole can be prepared by the following reaction scheme

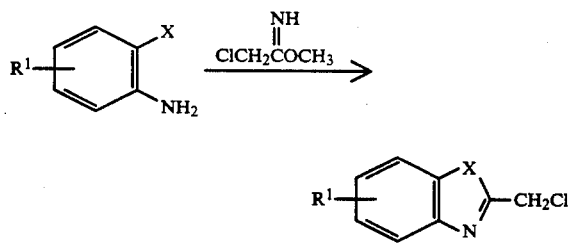

wherein X is O, S or NCH$_3$. The reaction is preferably carried out at a controlled low temperature in an organic solvent, such as methylene chloride.

The compounds of the invention, by virtue of their ability to inhibit the activity of PLA$_2$ enzyme, as well as that of lipoxygenase enzyme and to antagonize mediators arising from the enzymatic pathway, are useful in the treatment of conditions mediated by products of the oxidation of arachidonic acid. Accordingly, the compounds are indicated in the treatment of such diseases as rheumatoid arthritis, inflammatory bowel disease, osteoarthritis, tendinitis, bursitis, psoriasis (and related skin inflammation) and similar conditions involving inflammation. Moreover, by virtue of their ability to antagonize the effect of LTC$_4$, LTD$_4$ and LTE$_4$, which are the constituents of SRS-A, they are useful for the inhibition of symptoms induced by these leukotrienes. Accordingly, the compounds are indicated in the prevention and treatment of those disease states in which LTC$_4$, LTD$_4$ and LTE$_4$ are causative factors, for example allergic rhinitis, allergic bronchial asthma and other leukotriene mediated nasobronchial obstructive air-passageway conditions, as well as in other immediate hypersensitivity reactions, such as allergic conjunctivitis. The compounds are especially valuable in the prevention and treatment of allergic bronchial asthma.

The compounds of the invention are cytoprotective agents and are considered especially useful when administered with conventional non-steroidal anti-inflammatory drugs, whose major side effect is gastrointestinal irritation. The cytoprotective effect of the compounds of the invention significantly reduces the gastroirritant impact of conventional anti-inflammatory drugs. This effect is based not only on the ability of the compounds of the invention to inhibit the biological effects of leukotrienes and/or control the biosynthesis of these substances, as by inhibiting lipoxygenase, but also by a shunting effect, whereby the control of the lipoxygenase pathway "shunts" the oxidation of arachidonic acid into the cyclooxygenase pathway, giving rise to an increase in the formation of cytoprotective prostaglandins. These biological effects make the compounds of the invention especially useful in treating such conditions as erosive esophagitis, inflammatory bowel disease and induced hemorrhagic lesions such as those induced by alcohol or non-steroidal anti-inflammatory drugs (NSAID's), hepatic ischemia, noxious agent induced damage or necrosis of hepatic, pancreatic, renal or myocardial tissue; liver parenchymal damage caused by hepatotoxic agents such as carbon tetrachloride and D-galactosamine; ischemic renal failure; disease-induced hepatic damage; bile salt-induced pancreatic or gastric damage; trauma or stress-induced cell damage; and glycerol-induced renal failure.

When the compounds of the invention are employed in the treatment of allergic airway disorders, as anti-inflammatory agents and/or as cytoprotective agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The $PLA_2$ and lipoxygenase inhibitory and leukotriene antagonist effects, as well as the anti-inflammatory and potential gastroirritant effects of the compounds of the invention, may be demonstrated by standard pharmacological procedures which are described more full in the examples given hereinafter.

These procedures, inter alia, determine the specificity of action of the compounds of the invention as $PLA_2$ inhibitors as measured by their ability to inhibit the synthesis of $LTB_4$ and $PGE_2$ by rat glycogen-elicited polymorphonuclear leukocytes, as well as measure their ability to inhibit arachidonic acid release mediated by human source $PLA_2$. The pharmacological testing additionally demonstrates the ability of the compounds of the invention to inhibit, in vivo, the lipoxygenase and cyclooxygenase pathways of arachidonic acid metabolism; their ability to inhibit 5-lipoxygenase in human whole blood; their ability to antagonize $LTD_4$-induced contractions of isolated guinea pig trachea; and their ability to inhibit $LTB_4$ biosynthesis by purified human neutrophils.

The following examples show the preparation and pharmacological testing of compounds within the invention.

EXAMPLE 1

1-[2-Nitro-4'-(2-quinolinylmethoxy)-[1,1'-biphenyl]4-yl]ethanone

A. 4-Acetyl-4'-methoxy-2-nitro biphenyl

A stirred mixture of 4-iodoanisole (43.65 g, 0.187 mole), 4-bromo-3-nitro acetophenone (40.6 g, 0.166 mole) and copper powder (copper bronze, 36 g, 0.567 mole) kept under nitrogen is placed in an oil bath heated at 80° C. The temperature is slowly raised to 110° C. and the mixture is kept at this temperature for 5 days (TLC, 8:2 hexane-ethyl acetate). Upon cooling the mixture is dissolved in dichloromethane and filtered through a Celite pad. The filtrate and washing are evaporated and the residual thick, dark brown oil (58.4 g) is flash chromatographed (on silica Merck 60, preabsorbed in dichloromethane, eluted with 9:1 hexane-ethyl acetate to remove the impurities and 8:2 hexane-ethyl acetate to recover the main product) to provide 16.2 g (32%) of the title compound (yellow solid, m.p.124°–126° C.).

NMR ($CDCl_3$, 400 MHz): δ2.67 (s,3H, $COCH_3$), 3.85 (s, 3H, $OCH_3$), 6.97 (d, 2H, J 8.74 Hz, ArH), 7.27 (d, 2H, J 8.74 Hz, ArH), 7.56 (d, 1H, J 8 Hz, ArH), 8.15 (d, 1 H, J 8 Hz, ArH), 8.34 (s, 1H, ArH)

MS (EI, m/z): 271 (M)+.

B. 4-Acetyl-4'-hydroxy-2-nitro biphenyl

To a stirred solution of $AlBr_3$ (12.6 g, 47.4 mmole) in benzene (45 mL) is added dropwise under nitrogen a solution of the methylether (5 g, 18.45 mmole) of Step A in benzene (12 mL) over 30 minutes. The resulting solution is stirred at room temperature for 3.5 hours. (TLC, 8:2 hexane-ethyl acetate). The mixture is cooled in an ice bath and the complex is decomposed by the dropwise addition of 6N-HCl (ca. 37 mL). The organic layer is separated and the aqueous phase is reextracted with ether (3×). The combined extracts are concentrated to a small volume and extracted again with 2.5N-NaOH (2×50 mL +1×10 mL). The basic extracts are cooled and acidified with concentrated HCl (to pH 2). The solid is collected and dried (4.27 g, 90%). It is used in the next step without further purification.

NMR ($CDCl_3$, 400 MHz): δ2.67 (s, 3H, $COCH_3$), 5.03 (broad, 1H, OH), 6.91 (d, 2H, J 8.56 Hz, ArH), 7.23 (d, 2H, J 8.57 Hz, ArH), 7.55 (d, 1H, J 7.9 Hz, ArH), 8.15 (d, 1H, J 8.1 Hz, ArH), 8.34 (s, 1H, ArH).

MS (EI, m/z): 257 (b.p.,M)+.

C. 1-[2-Nitro-4'-(2-quinolinyl)[1,1'-biphenyl-4-yl]ethanone

A mixture of the phenol (4.4 g, 17.12 mmole) of Step B, powdered anhydrous potassium carbonate (2.37 g, 17.12 mmole), 18-crown-6 (0.453 g, 1.71 mmole) and acetonitrile (38 mL) is stirred at room temperature under nitrogen for 15 minutes. 2-Chloromethylquinoline (3.34 g, 18.83 mmole, free base freshly prepared from the hydrochloride salt) is added and the mixture is refluxed for 10 hours. (TLC, 7:3 hexane-ethyl acetate). A 10% excess of potassium carbonate, 18-crown-6 and the chloromethylquinoline is added and reflux continued for another 4 hours. The solvent is removed and the residue is diluted with water and extracted with ethyl acetate (3×). The extracts are washed and dried ($MgSO_4$). The residue is flash chromatographed (on silica Merck 60, preabsorbed in dichloromethane and eluted in order of increasing polarity with 7:3, 1:1 and 1:3 hexane-ethyl acetate followed by pure ethyl acetate) to provide the pure title compound (2.59 g). Recrystallization from toluene yields a yellow solid, m.p. 160°–162° C. (2.05 g, 30%).

NMR ($CDCl_3$, 400 MHz): δ2.66 (s, 3H, $COCH_3$), 5.43 (s, 2H, $OCH_2Ar$), 7.10 (d, 2H, J 8.7 Hz, ArH), 7.27 (d, 2H, J 8.7 Hz, ArH), 7.56 (m, 2H, ArH), 7.68 (d, 1H, J 8.49 Hz, ArH), 7.75 (dt, 1H, ArH), 7.84 (d, 1H, J 8.1 Hz, ArH), 8.09 (d, 1H, J 8.5 Hz, ArH), 8.14 (dd, 1H, ArH), 8.22 (d, 1H, J 8.49 Hz, ArH), 8.34 (s, 1H, ArH).

MS (EI, m/z): 398 (M)+, 256,158,142 (b.p.).

Analysis for: $C_{24}H_{18}N_2O_4$: Calculated: C, 72.35; H, 4.55; N, 7.03. Found: C, 71.96; H, 4.75; N, 6.80.

EXAMPLE 2

2-Fluoro-4'-(2-quinolinylmethoxy)-[1,1'-biphenyl]-4-acetic acid

A. 4-Acetyl-4'-methoxy-2-amino biphenyl

To a stirred, warm solution of tin (II) chloride (49.4 g, 218.9 mmole) in a mixture of concentrated HCl (72 mL) and ethanol (99 mL) is added over a period of 45 minutes the nitro derivative (10.7 g, 39.5 mmole) of Example 1A. The resulting yellow solution is refluxed for 3.5 hours (TLC, 1:1 hexane-ethyl acetate). The ethanol is removed and the residue is poured into a mixture of 50% NaOH (360 mL) and ice. The resulting solid is extracted (dichloromethane, 3×), the extracts are washed with water and dried ($Na_2SO_4$). Removal of the solvent provides a yellow solid (9.31 g, 97.8%), m.p. 152°-154° C.

NMR ($CDCl_3$, 400 MHz): δ2.59 (s, 3H, $COCH_3$), 3.80 (s, 3H, $OCH_3$), 6.97 (d, 2H, J 8.7 Hz, ArH), 7.23 (d, 1H, J 7.4 Hz, ArH), 7.40 (d, 2H, J 8.7 Hz, ArH), 7.48 (d, 1H, J 7.3 Hz, ArH), 7.49 (s, 1H, ArH).

MS (EI, m/z): 241 (b.p., M)+, 226 (M-$CH_3$)+, 198 (M-$COCH_3$)+, 83.

B. 4-Acetyl-4'-methoxy-2-fluoro biphenyl

To a stirred, ice cold mixture of the aniline (9.2 g, 38.2 mmole) in tetrahydrofuran (26 mL), water (9.8 mL) and $HBF_4$ (48%, 35.1 mL) is slowly added a solution of sodium nitrite (2.82 g, 40.85 mmole) in water (5 mL). The internal temperature is kept below 5° C. during the addition. The mixture is then stirred for an additional 20 minutes at 0°-5° C. The diazonium fluoroborate is filtered off and washed with 10% $HBF_4$ and 10% methanol in ether and dried in vacuo. The salt is decomposed by heating at 70° C. in xylene (95 mL). When the decomposition subsides, the mixture is refluxed for another 2.5 hours (TLC, 1:1 hexane-ethyl acetate, UV). The xylene is removed and the residue is extracted with ethyl acetate (3×) and ether. The combined extracts are washed with 10% sodium carbonate and brine and dried ($MgSO_4$). Removal of the solvent provides an amber oil (6.03 g) which is purified by flash chromatography (on silica Merck 60, preabsorbed in dichloromethane and eluted with 95:5 hexane-ethyl acetate). The title compound is obtained as a yellow solid 3.12-4.75 g, (33-51% depending on the run); m.p. 100°-101° C.

NMR ($CDCl_3$, 400 MHz): δ2.62 (s, 3H, $COCH_3$), 3.86 (s, 3H, $OCH_3$), 7.00 (d, 2H, J 8.9 Hz, ArH), 7.50-7.80 (m, 5H, ArH).

MS (EI, m/z): 244 (M)+, 229 (b.p., M-CH3)+.

C. 2-Fluoro-4'-methoxy-[1,1'-biphenyl]-4-acetic acid

A mixture of sulfur (0.468 g, 14.6 mmole), morpholine (2.57 mL) and the ketone (3.95 g, 16.2 mmole) of Step A is refluxed for 17 hours (TLC, acid treated silica plate, 8:2 hexane-ethyl acetate). Upon cooling, glacial acetic acid (9.9 mL), sulfuric acid (1.6 mL) and water (4 mL) are added and the reflux resumed for 30 hours. Water is then added and the mixture is extracted with ether (3×). The combined extracts are concentrated to a smaller volume and extracted with 10% sodium carbonate. The basic extracts are carefully acidified in the cold with concentrated HCl (to pH 2). The title acid is extracted with ether (3×) and the extracts are washed and dried ($MgSO_4$). Removal of the solvent provides a tan to brown solid (2.37 g, 56.3%) melting at 140°-142° C.

NMR ($CDCl_3$, 400 MHz): δ3.68 (s, 2H, $CH_2COO$), 3.85 (s, 3H, $OCH_3$), 6.96-7.50 (m, 7H, ArH).

MS (EI, m/z): 260 (M)+, 215 (b.p., M-COOH)+.

D. 2-Fluoro-4'-hydroxy-[1,1'-biphenyl]-4-acetic acid

To a solution of the methylether (1.31 g, 5.04 mmole) of Step C in glacial acetic acid (17 mL) is added dropwise 48% HBr in acetic acid (25 mL) and the mixture is refluxed for 4.5 hours (TLC, 7:3 hexane-ethyl acetate). A little water is added and the mixture is extracted with ether (3×). The extracts are washed and dried ($MgSO_4$). Removal of the solvent provides the title compound as a tan solid (1.13 g, 92%), m.p. 208°-210° C.

NMR (DMSO-$d_6$, 400 MHz): δ3.61 (s, 2H, $CH_2COO$), 6.83 (d, 2H, J 8.64 Hz, ArH), 7.1-7.42 (m, 5H, ArH), 9.61 (s, 1H, COOH).

MS (CI, m/z): 246 (M)+, 201 (b.p., M-COOH)+.

E. 2-Fluoro-4'-hydroxy-[1,1'-biphenyl]-4-acetic acid methylester

A solution of the acid (1.1 g, 4.47 mmole) of Step D in methanol (10 mL) containing p-toluenesulfonic acid. $H_2O$ (0.159 g) is refluxed for 1.5 hours (TLC, acid treated silica plate, hexane-ethyl acetate 7:3). The solvent is removed, the residue is dissolved in ethyl acetate, washed with brine and dried ($MgSO_4$). The tan solid (1.16 g, m.p. 115°-118° C., quantitative yield) is used as such in the next step.

NMR ($CDCl_3$, 400 MHz): δ3.65 (s, 2H, $CH_2COO$), 3.73 (s, 3H, $COOCH_3$), 6.88 (d, 2H, J 8.8 Hz, ArH), 7.10 (m, 2H, ArH), 7.32-7.44 (m, 3H, ArH).

MS (EI, m/z): 260 (M)+, 201 (b.p., M-$COOCH_3$)+.

F. 2-Fluoro-4'-(2-quinolinylmethoxy)-[1,1'-biphenyl]-4-acetic acid methylester

A stirred mixture of the phenol (1.16 g, 4.46 mmole) of Step E, powdered anhydrous potassium carbonate (0.616 g, 4.46 mmole), 18-crown-6 (0.118 g, 0.445 mmole) and acetonitrile (10 mL) is stirred at room temperature under nitrogen for 15 minutes. 2-Chloromethylquinoline (0.871 g, 4.9 mmole, free base freshly prepared from the hydrochloride salt) is then added and the mixture is placed in an oil bath heated at 65° C. for 5 hours. A 10% excess of potassium carbonate, 18-crown-6 and the chloromethylquinoline is added and the heating continued for another 6 hours (TLC, 19:1 dichloromethane-methanol or 7:3 hexane-ethyl acetate). The solvent is removed and the residue is diluted with water and extracted with ethyl acetate (3×). The extracts are washed and dried ($MgSO_4$). Removal of the solvent provides a tan solid which is purified by flash chromatography (on silica Merck 60, preabsorbed with dichloromethane, eluted with 7:3 hexane-ethyl acetate). The title compound thus obtained (1.55 g, 87%) is recrystallized from methanol. The off-white solid melts at 99°-101° C.

NMR ($CDCl_3$, 400 MHz): δ3.64 (s, 2H, $CH_2COO$), 3.72 (s, 3H, $COOCH_3$), 5.43 (s, 2H, $OCH_2Ar$), 7.1 (m, 4H, ArH), 7.35 (t, 1H, ArH), 7.47 (d, 2H, ArH), 7.55 (t, 1H, ArH), 7.69 (d, 1H, ArH), 7.74 (t, 1H, ArH), 7.84 (d, 1H, ArH), 8.09 (d, 1H, ArH), 8.20 (d, 1H, ArH).

MS (EI, m/z): 401 (M)+, 142, 114 (b.p.).

Analysis for: $C_{25}H_{20}FNO_3$: Calculated: C, 74.80; H, 5.02; N, 3.49. Found: C, 74.68; H, 4.65; N, 3.49.

G. 2-Fluoro-4'-(2-quinolinylmethoxy)-[1,1'-biphenyl]-4-acetic acid

A solution of the ester (1.69 g, 4.21 mmole) of Step F, in dry tetrahydrofuran (20 mL) is treated dropwise under nitrogen with 1N-LiOH (12.6 mL) and the mixture is stirred for 3 hours at room temperature (TLC, 19:1 dichloromethane-methanol or 1:1 hexane-ethyl acetate). The solvent is removed, the residue is treated with water and neutralized (to pH 6.5) with 10% acetic acid. The acid is extracted with ethyl acetate (large volume needed) and the extracts are dried ($MgSO_4$) and evaporated to dryness to yield an off-white solid (1.65 g, quantitative yield, m.p. 190°-193° C., dec.). Recrystallization from ethyl acetate provides a white solid (1.32 g, 80%, m.p. 195°-196° C. dec.). The analytical sample is dried in vacuo at 40° C.

NMR (DMSO-d$_6$, 400 MHz): δ3.62 (s, 2H, CH$_2$COO), 5.41 (s, 2H, CH$_2$OAr), 7.15 (m, 4H, ArH), 7.41 (t, 1H, J 8 Hz, ArH), 7.48 (d, 2H, ArH), 7.61 (t, 1H, ArH), 7.69 (d, 1H, ArH), 7.78 (dt, 1H, ArH), 8.01 (m, 2H, ArH), 8.42 (d, 1H, ArH), 12.42 (s, COOH).

MS (+FAB, m/z): 388 (M)+.

Analysis for: C$_{24}$H$_{18}$FNO$_3$:

Calculated: C, 74.41; H, 4.68; N, 3.62.

Found: C, 74.28; H, 4.48; H, 3.69.

EXAMPLE 3

3-[4-(2-Quinolinylmethoxy)benzoyl]benzene acetic acid

A. 3-Methyl-[4'-methoxy]-benzophenone

A 3-neck flask equipped with a condenser, mechanical stirrer and dropping funnel is charged under nitrogen with 1.925 g (79.19 g.a.) of magnesium turnings and enough ether to cover the turnings. A few drops of a solution of 3-bromotoluene (15.79 g, 92.28 mmole) in ether (40 mL) is then added along with a crystal of iodine to initiate the reaction. The remainder of the solution is then added dropwise and the mixture is refluxed until most of the magnesium has disappeared. After cooling, a solution of 4-methoxybenzonitrile (10 g, 75.1 mmole, dried in vacuo over P$_2$O$_5$) is added in one portion. The mixture is refluxed for 2 hours (TLC, no starting material present), cooled (ice bath) and slowly treated with cold water (130 mL) followed by dilute H$_2$SO$_4$ (1:1, v/v, 25 mL). The decomposition of the complex is completed by refluxing the mixture for 4 hours (followed by TLC, 8:2 ether-ethyl acetate). Following stirring overnight at room temperature, the layers are separated and extracted with ether (3×). The extracts are washed with 5% NaHCO$_3$, dried (MgSO$_4$) and evaporated to dryness. The crude material (amber oil, 13.93 g) is purified by flash chromatography (on silica Merck-60, eluted with 8:2 petrolether-ethyl acetate) to provide the title compound as a light yellow oil (12.5 g, 73.5%).

NMR (CDCl$_3$, 400 MHz): δ2.4 (s, 3H, CH$_3$), 3.9 (s, 3H, OCH$_3$), 6.96 (d, J 8.8 Hz, 2H, ArH), 7.38 (m, 2H, ArH), 7.53 (d, J 6.9 Hz, 1H, ArH), 7.57 (s, 1H, ArH), 7.82 (d, J 8.7 Hz, 2H, ArH).

MS (EI, m/z): 226 (M)+, 135 (b.p.), 91.

B. 3-Bromomethyl-[4'-methoxy]-benzophenone

A solution of the benzophenone (17.5 g, 77.4 mmole) of Step A in ethylene bromide (26.5 mL) (containing a small amount of benzoyl peroxide) is heated at reflux. A solution of bromine (12.7 g, 79.6 mmole) in ethylene bromide (15 mL) is added dropwise over 30 minutes while the mixture is irradiated with a Photolamp (300 W). Reflux is continued for 17 hours (TLC, 9:1 petrolether-ethylacetate, traces of starting material still present). The solvent is removed in vacuo and the residue (brown oil, 39.22 g) is purified by flash chromatography (on silica Merck-60, preabsorbed in dichloromethane, eluted with 9:1 petrolether-ethyl acetate) to give unreacted starting material (2.59 g, ca. 15%) along with the desired product (14.36 g, 61% or 71.5% based on recovered unreacted starting material) and some mixed fraction (ca. 5.20 g). The light yellow solid melts at 58°-61° C. and it is used as such in the next step.

NMR (CDCl$_3$, 400 MHz): δ3.88 (s, 3H, OCH$_3$), 4.52 (s, 2H, CH$_2$Br), 6.96 (d, J 8.8 Hz, 2H, ArH) 7.44 (t, J 7.6 Hz, 1H, ArH), 7.58 (d, J 7.8 Hz, 1H, ArH), 7.66 (d, J 7.6 Hz, 1H, ArH), 7.76 (s, 1H, ArH), 7.81 (d, J 8.8 Hz, 1H, ArH).

MS (EI, m/z): 306/304 (1 bromine, M)+, 225, 135 (b.p.). Trace of dibromo at 386/384/382 (possibly

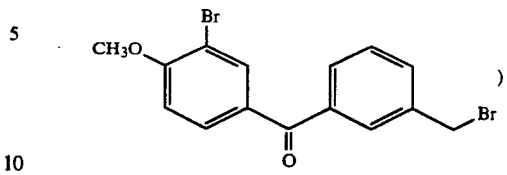

C. 3-Cyanomethyl-[4'-methoxy]-benzophenone

The bromo compound (14 g, 45.9 mmole) of Step B, is dissolved in dioxane (30 mL) and a solution of NaCN (7 g) in water (28.5 mL) is added. The mixture is refluxed for 6 hours (TLC, petrolether-ethyl acetate 8:2), charcoalized if needed and extracted with ether (3×). The extracts are dried (MgSO$_4$) and evaporated to dryness to yield a brown oil (13.44 g). The crude product is purified by flash chromatography (on silica Merck-60, preabsorbed in dichloromethane, eluted with 6:4 hexane-ethyl acetate) to provide the pure product (10.69 g, 92%) as a light yellow oil that sets up upon standing. The nearly colorless solid melts at 70°-71° C.

NMR (CDCl$_3$, 400 MHz): δ3.80 (s, 2H, CH$_2$CN), 3.87 (s, 3H, OCH$_3$), 6.95 (d, J 8.6 Hz, 2H, ArH), 7.48 (t, J 7.7 Hz, 1H, ArH), 7.54 (d, J 7.6 Hz, 1H, ArH), 7.68 (s+d, J 7.6 Hz, 2H, ArH), 7.79 (d, J 8.6 Hz, 2H, ArH).

MS (EI, m/z): 251 (M)+, 135 (b.p.).

D. 3-[4-Methoxybenzoyl]-phenylacetic acid

The nitrile (4 g, 15.9 mmole) of Step C, is dissolved in 40% NaOH (40 mL) and the solution is heated at reflux under nitrogen for 7 hours (TLC, toluene-methanol 9:1). Water is added while cooling in an ice bath. The solution is washed with ethyl acetate and then acidified in the cold with concentrated HCl (to pH 2). The acid is extracted with ethyl acetate (3×) and the extracts are dried (MgSO$_4$) and evaporated to dryness to yield the crude product (yellow solid, 3.56 g, 82%), m.p. 138°-140° C.

NMR (CDCl$_3$, 400 MHz): δ3.72 (s, 2H, CH$_2$COO), 3.88 (s, 3H, OCH$_3$), 6.95 (d, J 8.8 Hz, 2H, ArH), 7.43 (t, 1H, ArH), 7.48 (d, 1H, ArH), 7.65 (d, 1H, ArH), 7.68 (s, 1H, ArH), 7.81 (d, J 8.6 Hz, 2H, ArH).

MS (EI, m/z): 270 (M)+, 211 (M-CH$_2$COOH)+, 135 (b.p.), 107.

E. 3-[4-Hydroxybenzoyl]-phenylacetic acid

An intimate mixture of the acid (8.1 g, 0.030 mole) of Step D, and pyridine hydrochloride (13.87 g, 0.120 mole) is stirred under nitrogen in an oil bath heated at 200°-210° C. for 7 hours (TLC, toluene-methanol 9:1, dichloromethane-methanol 9:1). After cooling, the mixture is dissolved in dichloromethane. The solution is extracted with 1N-NaOH, the extract acidified in the cold with concentrated HCl and extracted with ethyl acetate (3×). After drying (MgSO$_4$) the solvent is removed to provide the crude title compound as a tan solid (7.61 g, quantitative yield), m.p. 147°-149° C.

NMR (DMSO-d$_6$, 400 MHz): δ3.67 (s, 2H, CH$_2$COO), 6.88 (d, J 8.84 Hz, 2H, ArH), ca. 7.5 (m, 4H, ArH), 7.65 (d, J 8.8 Hz, 2H, ArH), 10.4 (s, 1H, OH), ca. 12.3 (s, 1H, COOH).

MS (m/z): 257 (M+H)+, 217, 131, 91 (b.p.).

F. 3-[4-Hydroxybenzoyl]-phenylacetic acid methylester

A mixture of the acid (8.56 g, 33.4 mmole) of Step E and p-toluenesulfonic acid monohydrate (1.05 g, 5.6 mmole) in methanol (70 mL) is refluxed for 2.5 hours (TLC, methanol-toluene 1:9). The methanol is evaporated and the residue is dissolved in ethyl acetate and washed with brine. After drying (MgSO₄) the solvent is removed to yield a tan solid (8.68 g, 96.2%, m.p. 111°–113° C.). The crude product is used as such in the next step.

NMR (CDCl₃, 400 MHz): δ3.69 (s, 2H, CH₂COO), 3.69 (s, 3H, COOCH₃), 6.86 (d, J 8.4 Hz, 2H, ArH), 7.41 (t, 1H, 7.58 Hz, 1H, ArH), 7.47 (d, J 7.56 Hz, 1H, ArH), 7.62 (d, J 7.4 Hz, 1H, ArH), 7.64 (s, 1H, ArH), 7.74 (d, 2H, J 8.4 Hz, ArH).

MS (m/z): 271(M+H)+, 217, 131, 91 (b.p.).

G. 3-[4-(2-Quinolinylmethoxy)benzoyl]benzene acetic acid methylester

A mixture of the phenol (4 g, 14.8 mmole) of Step F, powdered anhydrous K₂CO₃ (2.05 g, 14.8 mmole) and 18-crown-6 (0.4 g, 1.48 mmole) in acetonitrile (35 mL) is stirred at room temperature under nitrogen for 15 minutes. 2-Chloromethylquinoline (2.9 g, 16.28 mmole, freshly prepared from the hydrochloride salt) is added in one portion and the mixture is heated in an oil bath kept at 65°–70° C. for 8 hours (TLC, toluene-methanol 9:1). A 10% excess of K₂CO₃, crown ether and chloromethylquinoline is added and the heating is continued for another 8 hours. The acetonitrile is evaporated and the residue is partitioned between water and ethyl acetate. The organic layer is dried (MgSO₄) and evaporated to yield a tan solid (6.57 g). The crude product is purified by flash chromatography (on silica Merck-60, preabsorbed in dichloromethane, eluted with petrolether-ethyl acetate 7:3) to give the title compound as a light yellow solid (5.03 g, 82.7%) m.p. 93°–95° C.

NMR (CDCl₃, 400 MHz): δ3.67 (s,5H, CH₂COO +OCH₃), 5.45 (s, 2H, ArCH₂O), 7.08 (d, J 8.8 Hz, 2H, ArH), 7.40 (t, J 7.8 Hz, 1H, ArH), 7.46 (d, J 7.7 Hz, 1H, ArH), 7.55 (t, J 7.3 Hz, 1H, ArH), 7.6–7.66 (m, 3H, ArH), 7.7–7.82 (m, 4H, ArH), 8.07 (d, 1H, ArH), 8.20 (d, J 8.4 Hz, 1H, ArH).

MS (EI, m/z): 411 (M)+, 142, 121 (b.p.).

H. 3-[4-(2-Quinolinylmethoxy)benzoyl]benzene acetic acid

To a solution of the ester (5 g, 12.16 mmole) of Step G, in dry tetrahydrofuran (66 mL) is added 1N-LiOH (37 mL, 37 mmole) and the mixture is stirred under nitrogen at room temperature for 2.5 hours (TLC, toluene-MeOH 9:1). The tetrahydrofuran is evaporated and the residue is diluted with water, acidified (to pH 6.5) with 10% acetic acid and extracted with ethyl acetate (3×). The extracts are washed with brine, dried (MgSO₄) and evaporated to dryness. The crude product (4.94 g, pale yellow solid) is recrystallized from ethyl acetate to provide 3.65 g (75%) of the pure title compound (white solid, m.p. 146°–147° C.).

NMR (DMSO-d₆, 400 MHz): δ3.68 (s, 2H, CH₂COO), 5.48 (s, 2H, ArCH₂O), 7.22 (d, 2H, J 8.8 Hz, ArH), 7.47 (m, 1H, ArH), 7.53 (m, 2H, ArH), 7.62 (m, 2H, ArH), 7.69 (d, J 8.4 Hz, 1H, ArH) 7.74–7.82 (m, 3H, ArH), 8.2 (m, 2H, ArH), 8.43 (d, J 8.5 Hz, 1H, ArH), 12.39 (1H, COOH).

MS (EI, m/z): 397 (b.p., M)+, 380 (M-OH)+, 142.

Analysis for: C₂₅H₁₉NO₄ Calculated: C, 75.57; H, 4.78; N, 3.53. Found: C, 75.22; H, 4.76; N, 3.39.

EXAMPLE 4

3-[4-(2-Naphthalenylmethoxy)benzoyl]benzene acetic acid

A. 3-[4-(2-Naphthalenylmethoxy)benzoyl]benzene acetic acid methylester

A mixture of the phenol (1 g, 3.7 mmole) of Example 3F, powdered anhhydrous K₂CO₃ (0.48 g, 3.7 mmole), 18-crown-6 (0.098 g, 0.37 mmole) and acetonitrile (10 mL) is stirred under nitrogen for 15 minutes. 2-Bromomethylnaphthalene (0.496 g, 4.07 mmole) is added and the mixture is placed in an oil bath heated at 65°–70° C. for 10 hours (TLC, dichloromethane-ethyl acetate 8:2). A 10% excess of K₂CO₃, crown ether and bromomethylnaphthalene is added and the heating is continued for another 4 hours. The acetonitrile is evaporated and the residue dissolved in water and extracted with ethyl acetate (3×). The extracts are washed with 1N-NaOH and brine, dried (MgSO₄) and evaporated to dryness. The crude product (1.49 g, waxy solid) is used as such in the next step.

NMR (CDCl₃, 400 MHz): δ3.7 (s, 5H, OCH₃+CH₂COO), 5.32 (s, 2H, ArCH₂O), 7.08 (d, J 8.7 Hz, 2H, ArH), 7.4–7.56 (m, 5H, ArH), 7.63–7.68 (m, 2H, ArH), 7.82–7.92 (m, 6H, ArH).

MS (m/z): 410 (M)+, 141 (b.p.).

B. 3-[4-(2-Naphthalenylmethoxy)benzoyl]benzene acetic acid

A solution of the ester (1.29 g, 3.15 mmole) of Step A, is treated dropwise with 1N-LiOH and the mixture is stirred under nitrogen overnight. The solvent is evaporated and the residue is dissolved in water, acidified in the cold with 10% acetic acid (to pH 3) and extracted with ethyl acetate (3×). The extracts are dried (MgSO₄) and evaporated to dryness. The residue (1.24 g, quantitative yield) is recrystallized by dissolving it in a relatively large volume of warm ethyl acetate-dichloromethane followed by concentrating to half volume. The precipitate is collected and dried at 45° C. in vacuo (0.610 g, 48.8%), m.p. 150°–152° C.

NMR (DMSO-d₆, 400 MHz): δ3.70 (s, 2H, CH₂COO), 5.40 (s, 2H, ArCH₂), 7.20 (d, 2H, ArH), 7.45–7.60 (m, 7H, ArH), 7.75 (d, 2H, ArH), 7.95 (m, 3H, ArH), 8.02 (s, 1H, ArH), 12.47 (broad s, 1H, COOH).

MS (+FAB, m/z): 397 (M+H)+, 217, 141.

Analysis for: C₂₆H₂₀O₄Calculated: C, 78.78; H, 5.09. Found: C, 78.12; H, 5.13.

EXAMPLE 5

5-Phenyl-4-[4-(2-Quinolinylmethoxy)phenyl]-2-oxazole propanoic acid

A. 4-Methoxybenzoin

To a solution of KCN (5 g) in water (35 mL) is added 4-methoxybenzaldehyde (27.2 g, 0.2 mole), benzaldehyde (21.2 g, 0.2 mole) and 95% ethanol (70 mL). The mixture is refluxed under nitrogen for 4.5 hours and the ethanol removed in vacuo. Water (200 mL) is added to the residue and then distilled off at reduced pressure (to remove remaining unreacted bezaldehyde). The procedure is repeated twice and the residual water azeotroped with ethanol. The crude product (56.3 g, orange semi-solid) is purified by flashchromatography (on silica Merck-60, preabsorbed in dichloromethane-ethyl acetate and eluted with hexane-ethyl acetate 8:2) to yield a light yellow solid (20.1 g, 41.5%), m.p. 99°–101° C.

NMR (CDCl₃, 400 MHz): δ3.82 (s, 3H, OCH₃), 4.62 (broad s, 1H, OH), 5.88 (s, 1H, CHOH), 6.86 (d, 2H, J 8.94 Hz, ArH), 7.22-7.38 (m, 5H, ArH), 7.91 (d, 2H, J 8.94 Hz, ArH).

MS (CI, m/z): 243 (b.p., M+H)+, 225, 197, 137 (M-PhCO)+.

B. 4-Methoxybenzoin hemisuccinate

A mixture of 4-methoxybenzoin (20 g, 0.083 mole) and succinic anhydride (9.1 g, 0.091 mole) in toluene (6 mL) is heated for 7 hours under nitrogen at 135° C. (internal temp.). The solution is poured into 0.5 N-NaHCO$_3$, the organic layer was separated and reextracted with 0.5 N-NaHCO$_3$. The combined extracts are washed with ether and then acidified in the cold with concentrated HCl. The liberated oil is extracted with ethyl acetate (3×), the extracts washed with water and dried (MgSO$_4$). Removal of the solvent yields a yellow solid (20.89 g, 73.8%), m.p. 104°-108° C. It is used in the next step without further purification.

NMR (CDCl$_3$, 400 MHz): δ2.72-2.82 (mm, 4H, CH$_2$CH$_2$COO), 3.82 (s, 3H, OCH$_3$), 6.86 (d, 2H, J 9.1 Hz, ArH), 7.34-7.46 (m, 5H, ArH), 7.92 (d, 2H, J 9.1 Hz, ArH).

MS (EI, m/z): 342 (M)+, 135 (b.p.).

C. 4-(4-Methoxyphenyl)-5-phenyl-2-oxazole-propanoic acid

A mixture of the crude 4-methoxybenzoin hemisuccinate (20.8 g, 0.061 mole) of Step B, urea (8.7 g, 0.146 mole) and acetic acid (60 mL) is heated at reflux under nitrogen for 5.5 hours. The mixture is cooled and poured into ice water. The liberated oil is extracted with ethyl acetate (3×). The extracts are washed with water until neutral and then extracted with saturated sodium carbonate. The combined aqueous extracts are carefully acidified in the cold with concentrated HCl and extracted with ethyl acetate. The organic extract is dried (MgSO$_4$) and evaporated to dryness to provide a waxy yellow oil (19.6 g). Purification of the residue by flash chromatography (on silica Merck-60, eluant: dichloromethane-ethyl acetate 8:2) yields a pale yellow solid (14.3 g, 72.7%), m.p. 100°-101° C.

NMR (CDCl$_3$, 400 MHz): δ2.96 (t, 2H, CH$_2$C), 3.20 (t, 2H, CH$_2$COO), 3.83 (s, 3H, OCH$_3$), 6.90 (d, 2H, ArH), 7.28-7.38 (m, 3H, ArH), 7.54-7.62 (m, 4H, ArH).

MS (EI, m/z): 323 (M)+, 278 (b.p., M-COOH)+, 152, 77.

D. 4-(4-Hydroxyphenyl)-5-phenyl-2-oxazole-propanoic acid

To a solution of the methoxyacid (5.6 g, 17.3 mmole) of Step C, in acetic acid (55 mL) is added 48% HBr (84 mL) and the mixture is heated at reflux under nitrogen for 8 hours (TLC, 1:1 hexane-ethyl acetate). After cooling, water is added and the solution extracted with ethyl acetate (3×). The extract is dried (MgSO$_4$) and evaporated to dryness. The residue (brown waxy oil, 5.25 g, 99%) is used in the next step without further purification. For analytical characterization a small sample is flash-chromatographed (on silica Merck-60, eluant: dichloromethane-methanol 98:2 and 95:5).

NMR (DMSO-d$_6$, 400 MHz): δ2.75 (t, 2H, J 7.14 Hz, CH$_2$C), 3.02 (t, 2H, J 7.1 Hz, CH$_2$COO), 6.77 (d, 2H, J 8.7 Hz, ArH), 7.35 (d, 2H, J 8.55 Hz, ArH), 7.41 (t, 3H, J 7.12 Hz, ArH), 7.50 (d, 2H, J 7 Hz, ArH), 9.64 (broad s, exchangeable).

MS (EI, m/z): 309 (M)+, 264 (M-COOH)+, 121, 105, 77.

E. 5-Phenyl-4-(4-hydroxyphenyl)-2-oxazole propanoic acid methylester

A solution of the crude acid (5 g, 16.18 mmole) of Step D, in methanol (40 mL), containing a small amount of p-toluenesulfonic acid ·H$_2$O (0.58 g) is refluxed for 2.5 hours. The methanol is evaporated and the residue is partitioned between ethyl acetate and 20% NaCl. The extracts are washed, dried (MgSO$_4$) and evaporated to yield a thick oil (ca. 4.8 g). The residue is flash-chromatographed (on silica Merck-60, preabsorbed in dichloromethane, eluted with a dichloromethane-ethyl acetate gradient from 90:10 to 75:25) to yield a white solid (3.56 g, 68%), m.p. 115°-116° C.

NMR (CDCl$_3$, 400 MHz): δ2.92 (t, 2H, J 7.4 Hz, CH$_2$C), 3.20 (t, 2H, J 7.4 Hz, CH$_2$COO), 3.71 (s, 3H, OCH$_3$), 6.74 (d, 2H, J 8.59 Hz, ArH), 7.26-7.36 (m, 3H, ArH), 7.40 (d, 2H, J 8.7 Hz, ArH), 7.54 (d, 2H, J 7.56 Hz, ArH).

MS (EI, m/z): 323 (M)+, 264 (M-COOCH$_3$)+, 105, 77 (b.p.).

F. 5-Phenyl-4-[4-(2-quinolinylmethoxy)phenyl]-2-oxazole propanoic acid methylester A mixture of the ester (2.46 g, 7.61 mmole) of Step E, powdered anhydrous K$_2$CO$_3$ (1.05 g, 7.60 mmole), 18-crown-6 (0.223 g, 0.843 mmole) and acetonitrile (33 mL, ex-sieves) is stirred at room temperature under nitrogen for 15 minutes. 2-Chloromethylquinoline (free base, freshly prepared from the hydrochloride salt, 1.35 g, 7.60 mmole) is added and the mixture is placed in an oil bath heated at 65° C. for 10 hours (N.B. A 10% excess of the chloromethylquinoline, 18-crown-6 and K$_2$CO$_3$ is added after 6 hours). The solvent is removed and the residue is partitioned between ethyl acetate and water. The extracts are washed (brine), dried (MgSO$_4$) and evaporated to yield a yellow solid. The crude product is flash chromatographed (on silica Merck-60, eluant: toluene and then toluene-methanol 97.5:2.5) to provide the title compound (3.5 g, quantitative yield).

NMR (CDCl$_3$, 400 MHz): δ2.90 (t, 2H, J ca. 7.2 Hz, CH$_2$C), 3.16 (t, 2H, J7.2 Hz, CH$_2$COO), 3.72 (s, 3H, OCH$_3$), 5.41 (s, 2H, ArCH$_2$O), 7.02 (d, 2H, J 8.8 Hz, ArH), 7.29-7.36 (m, ca. 4H, ArH), 7.54-7.84 (m, ca. 6H, ArH), 7.83 (d, 1H, J 8.1 Hz, ArH), 8.08 (t, 1H, J 8.5 Hz, ArH), 8.19 (d, 1H, J 8.5 Hz, ArH).

MS (+FAB, m/z): 487 (M+Na)+, 465 (M+H)+.

G. 5-Phenyl-4-[4-(2-quinolinylmethoxy)phenyl]-2-oxazole propanoic acid

A solution of the ester (3.4 g, 7.32 mmole) of Step F, in dry tetrahydrofuran (37 mL) is treated dropwise under nitrogen with 1N-LiOH (21.98 mL, 3 equiv.) and stirred at room temperature for 3 hours (TLC, dichloromethane-methanol 97:3 or toluene-methanol 95:5). The solvent is evaporated, the residue is dissolved in water, neutralized in the cold with 10% acetic acid (to pH 5.5-6) and extracted with ethyl acetate. The extracts are washed with brine, dried (MgSO$_4$) and evaporated to yield a pale yellow solid (3.18 g, quantitative yield). The crude product is recrystallized from warm ethyl acetate (containing enough dichloromethane to obtain a clear solution) to yield a first crop of crystals (2.63 g, m.p. dec. 192°-194° C.). A second crop is obtained by concentrating the mother liquors (0.327 g, m.p. dec. 192°-193° C.). The combined yield is 85.8%.

IR (KBr, cm$^{-1}$): 1720 (CO).

NMR (DMSO-d$_6$, 400 MHz): δ2.76 (t, 2H, J 7 Hz, CH$_2$C), 3.03 (t, 2H, J 7 Hz, CH$_2$COO), 5.38 (s, 2H, ArCH$_2$O), 7.11 (d, 2H, J 8.8 Hz, ArH), 7.36-7.56 (m, 7H, ArH), 7.61 (t, 1H, ArH), 7.69 (d, 1H, J 8.5 Hz, ArH), 7.78 (t, 1H, ArH), 8.00 (t, J 7.9 Hz, 2H, ArH), 8.42 (d, 1H, J 8.5 Hz, ArH).

MS (EI or CI, m/z): 451 (M+H)+, 310 (b.p.).

Analysis for: $C_{28}H_{22}N_2O_4$ Calculated: C, 74.65; H, 4.92; N, 6.22. Found: C, 74.20; H, 4.86; N, 6.00.

EXAMPLE 6

4-[4-[2-Naphthalenylmethoxy]phenyl]5-phenyl-2-oxazole propanoic acid

A. 4-[4-[2-Naphthalenylmethoxy]phenyl]-5-phenyl-2-oxazole propanoic acid methylester A mixture of the hydroxyester (1.5 g, 4.6 mmole) of Example 5E, powdered anhydrous $K_2CO_3$ (0.636 g, 4.6 mmole), 18-crown-6 (0.123 g, 0.46 mmole) and acetonitrile (18 mL) is stirred at room temperature under nitrogen for 15 minutes. 2-Bromomethylnaphthalene (1.13 g, 5.1 mmole) is added and the mixture is placed in an oil bath heated at 70° C. for 8–9 hours (TLC, hexane-ethyl acetate 9:1 or dichloromethane-methanol 9:1). The solvent is evaporated and the residue dissolved in water and extracted with ethyl acetate. The extracts are washed and dried ($MgSO_4$). Removal of the solvent yields a tan solid (2.17 g, quantitative yield). A sample is recrystallized from methanol (containing enough dichloromethane to obtain a clear solution) by concentrating to small volume and cooling in an ice bath. The white solid is collected and dried overnight in vacuo, m.p. 134°–135° C.

IR (KBr, $cm^{-1}$): 1740 (CO).

NMR ($CDCl_3$-400 MHz): δ2.89 (t, 2H, J 7.5 Hz, $CH_2C$), 3.16 (t, 2H, J 7.5 Hz, $CH_2COO$), 3.71 (s, 3H, $OCH_3$), 5.2 (s, 2H, $ArCH_2O$), 7.00 (d, 2H, J 8.6 Hz, ArH), 7.25–7.35 (m, 3H, ArH), 7.46–7.58 (m, 7H, ArH), 7.8–7.9 (m, 4H, ArH).

MS (CI, m/z): 464 $(M+H)^+$, 324.

Analysis for: $C_{30}H_{25}NO_4$: Calculated: C, 77.73; H, 5.44; N, 3.02. Found: C, 77.44; H, 5.36; N, 3.03.

B. 4-[4-(2-Naphthalenylmethoxy)phenyl]-5-phenyl-2-oxazole propanoic acid

A solution of the ester (1.49 g, 3.21 mmole) of Step A, in dry tetrahydrofuran (18 mL) containing 1N-LiOH (9.6 mL) is stirred under nitrogen overnight at room temperature (TLC, 75:25 hexane-ethyl acetate). The solvent is evaporated, the residue dissolved in water and acidified (to pH 5) with dilute HCl. The mixture is extracted with ethyl acetate, the extracts are dried ($MgSO_4$) and evaporated to yield the crude product (1.39 g, m.p. 145°–150° C.). For purification, it is dissolved in hot ethyl acetate (containing enough dichloromethane to obtain a clear solution), concentrated to half volume and precipitated with ether. The white solid melts at 151°–152° C. (1.07 g, 58%).

IR (KBr, $cm^{-1}$): 1720 (CO).

NMR (DMSO-$d_6$, 400 MHz): δ2.78 (t, 2H, $CH_2C$), 3.03 (t, 2H, J 7 Hz, $CH_2COO$), 5.29 (s, 2H, $ArCH_2O$), 7.10 (d, 2H, J 8.9 Hz, ArH), 7.34–7.60 (m, 10H, ArH), 7.90–8.00 (m, 4H, ArH), 12.28 (s, 1H, COOH).

MS (EI, m/z): 450 $(M+H)^+$, 310.

Analysis for: $C_{29}H_{23}NO_4$: Calculated: C, 77.48; H, 5.15; N, 3.11. Found: C, 76.40; H, 5.16; N, 3.04.

EXAMPLE 7

4-[4-[(1-Methyl 1 H-benzimidazol-2-yl)methoxy]phenyl]-5-phenyl-2-oxazole propanoic acid A. 4-[4-[(1-Methyl 1 H-benzimidazol-2-yl)methoxy]phenyl]-5-phenyl-2-oxazole propanoic acid methylester A mixture of the ester (0.5 g, 1.55 mmole) of Example 5E, powdered anhydrous $K_2CO_3$ (0.214 g, 1.55 mmole), 18-crown-6 (0.0416 g, 0.155 mmole) and acetonitrile (6 mL) is stirred under nitrogen at room temperature for 15 minutes. 2-Chloromethyl-1-methylbenzimidazole (0.307 g, 1.7 mmole) is added and the mixture is placed in an oil bath heated at 65°–70° C. for 4 hours (TLC, dichloromethane-ethyl acetate 9:1, iodine visualization). A 10% excess of $K_2CO_3$, 2-chloromethyl-1-methyl-benzimidazole and 18-crown-6 is added at this point and the heating continued for another 10 hours. The solvent is evaporated, the residue dissolved in water and extracted with ethyl acetate. The extracts are washed, dried ($MgSO_4$) and evaporated to dryness. The residue (1.64 g) is purified by flash-chromatography (on silica Merck-60, preabsorbed in dichloromethane containing a small amount of methanol, eluted with dichloromethane-ethyl acetate 8:2) to yield 1.03 g (71.2%) of a light yellow solid, m.p. 142°–144° C. (dec).

NMR ($CDCl_3$, 400 MHz): δ2.87 (t, 2H, J 7.1 Hz, $CH_2C$), 3.16 (t, 2H, J 7.8 Hz, $CH_2COO$), 3.72 (s, 3H, $COOCH_3$), 3.90 (s, 3H, $NCH_3$), 5.41 (s, 2H, $ArCH_2O$), 7.07 (d, 2H, J 8.8 Hz, ArH), 7.25–7.40 (m, 7H, ArH), 7.5–7.6 (m, 3H, ArH), 7.78 (d, 1H, ArH).

MS (+C I, m/z): 468 $(M+H)^+$, 324, 293, 147.

4-[4-[(1-Methyl-1H-benzimidazol-2-yl)methoxy]-5-phenyl-2-oxazole propanoic acid

A solution of the ester (1 g, 2.14 mmole) of Step A, in tetrahydrofuran (13 mL) containing 1N-LiOH (6.42 mL) is stirred under nitrogen at room temperature for 1 hour (TLC, dichloromethane-ethanol 9:1). The solvent is evaporated, water added and the pH adjusted to 6.5 with 10% acetic acid. The light yellow precipitate is collected, washed with water and dried in vacuo. It is redissolved in hot ethyl acetate (containing enough methanol to obtain a clear solution), concentrated to a smaller volume and cooled in an ice bath. The crystals are collected and dried (0.642 g, 66.2%, m.p. 222°–224° C.).

NMR (DMSO-$d_6$, 400 MHz): δ2.76 (t, 2H, J 7 Hz, $CH_2C$), 3.03 (t, 2H, J 7 Hz, $CH_2COO$), 3.86 (s, 3H, $NCH_3$), 5.43 (s, 2H, $ArCH_2O$), 7.14–7.66 (m, 13H, ArH).

MS (CI, m/z): 454 $(M+H)^+$, 147 (b.p.).

Analysis for: $C_{27}H_{23}N_3O_4$: Calculated: C, 71.51; H, 5.11; N, 9.27. Found: C, 71.62; H, 5.17; N, 9.40.

EXAMPLE 8

N-Hydroxy-N-methyl-2-fluoro-4'-(2-quinolinylmethoxy)-[1,1'-biphenyl]-4-acetamide To a solution of the acid of Example 2 (1.0 g, 2.58 mmol) in methylene chloride (20 ml) containing dimethylformamide (0.2 ml), 2.58 mmol) at 0° C. is added oxalyl chloride (0.506 ml, 5.80 mmol), dropwise. After the reaction mixture is stirred for 1 hour, it is added dropwise to a solution of N-methylhydroxylamine hydrochloride (0.861 g, 10.32 mmol) in triethylamine (1.87 ml, 13.41 mmol), tetrahydrofuran (10 ml) and water (2.0 ml) at 0° C. After overnight stirring, the reaction mixture is poured into 2N HCl, the ensuing solid is collected and recrystallized from ethanol. The crystals are then flash chromatographed eluting with ethyl acetate-hexane (3:2) followed by ethyl acetate-ethanol (99:1). The material at this point is still contaminated with a minor impurity which is removed by conversion of the material to the hydrochloride salt, followed by washing with ethyl acetate, basification and final extraction with ethyl acetate to afford white crystals, m.p. 153°–155° C.

Analysis for: $C_{25}H_{21}N_2O_3F$: Calculated: C, 72.10; H, 5.08; N, 6.73. Found: C, 71.95; H, 5.07; N, 6.39.

EXAMPLE 9

2-Fluoro-4'-(2-quinolinylmethoxy)[1,1'-biphenyl]-4-acetic acid, 2-amino-2-hydroxymethyl-1,3-propane diol A solution of the compound of Example 2 (3.17 g, 8.2 mmole) and 2-amino-2-hydroxymethyl-1,3-propane diol [TRIS, 0.99 g, 8.2 mmole] in 60 mL of methanol is concentrated to a syrup. Following dilution with ethylacetate (250 mL), the crystalline precipitate is collected and dried to give 3.18 g of the title salt. The product is micronized to a fine white powder, m.p. 168°–169° C. (77.5% yield).

Analysis for: $C_{28}H_{29}FN_2O_6$: Calculated: C, 66.13; H, 5.75; N, 5.51. Found: C, 65.75; H, 5.79; N, 5.49.

EXAMPLE 10

5-Phenyl-4-[4-quinolinylmethoxy)-phenyl]-2-oxazole propionic acid, 2-amino-2-hydroxymethyl-1,3-propane diol To a solution of the compound of Example 5 (0.359 g, 0.796 mmole) in boiling ethanol (35 mL) is added 2-amino-2-hydroxymethyl-1,3-propane diol [TRIS, 0.0965 g, 0.796 mmole] in 0.5 mL of water. After two hours, the mixture is refrigerated. The crystalline precipitate is collected and dried to give 0.396 g of the title salt, m.p. 170°–171° C.

Analysis for: $C_{32}H_{33}N_3O_7$: Calculated: C, 67.00; H, 5.75; N, 7.32. Found: C, 66.68; H, 5.77; N, 7.31.

EXAMPLE 11

4'-(2-Benzothiazolylmethoxy)-4-diphenylacetic acid, ethyl ester

A. 4'-Hydroxy-4-diphenylacetic acid, ethyl ester

A solution containing 4'-hydroxy-4-diphenylacetic acid (6.7 g, 28.0 mmol), absolute ethanol (300 ml) and concentrated sulfuric acid (5 ml) is refluxed for 2 hours. The reaction mixture is cooled to room temperature, concentrated under reduced pressure, diluted with water (200 ml) and extracted with ethyl acetate (200 ml; 3 times). The combined ethyl acetate extract is washed with 1N sodium hydroxide (200 ml), water (200 ml) and brine (200 ml), is dried over anhydrous magnesium sulfate and is concentrated under reduced pressure to afford 6.9 g of crude solids. The solids are purified by chromatography (silica gel; 30% ethyl acetate in hexane) to give 6.7 g (95.0%) of white crystalline product, m.p. 125°–127° C.

Analysis for: $C_{16}H_{16}O_3$: Calculated: C, 74.98; H, 6.29. Found: C, 74.62; H, 6.22.

B. 4'-(2-Benzothiazolylmethoxy)-4-diphenylacetic acid, ethyl ester

A slurry of 4'-hydroxy-4-diphenylacetic acid, ethyl ester (6.7 g, 26.0 mmol, Part A.) and cesium carbonate (9.0 g, 28.0 mmol) in dimethylsulfoxide (150 ml) is stirred at room temperature. After 30 minutes, 2-(chloromethyl)-benzothiazole (4.2 g, 27.0 mmol) is added and the mixture is stirred for 18 hours. The reaction mixture is poured into ice-water (200 ml) and is extracted with ethyl acetate (300 ml, 3 times). The combined ethyl acetate extract is washed sequentially with 0.1N sodium hydroxide (200 ml), water (200 ml) and brine (200 ml), is dried over anhydrous magnesium sulfate, and concentrated under reduced pressure to give 8.0 g of crude solids. The solids are purified by chromatography (silica gel, 30% ethyl acetate in hexane) to afford 4.0 g (39.2%) of white crystalline produce, m.p. 133°–134° C.

Analysis for: $C_{24}H_{21}NO_3S$: Calculated: C, 71.44; H, 5.25; N, 3.47. Found: C, 71.36; H, 5.25; N, 3.35.

EXAMPLE 12

4'-(Benzothiazolylmethoxyl)-4-diphenylacetic acid

A mixture of 4'-(benzothiazolylmethoxy)-diphenylacetic acid, ethyl ester (4.0 g, 10.0 mmol), 1N sodium hydroxide (15 ml, 15.0 mmol), methanol (200 ml) and tetrahydrofuran (200 ml) is refluxed for 18 hours. The reaction mixture is cooled, concentrated under reduced pressure, is diluted with water (500 ml) and with stirring, is acidified with 2N hydrochloric acid. After stirring for two hours, the product is collected by filtration and after vacuum drying, 3.8 g (99%) of solids is obtained. A portion of this material (0.5 g) is recrystallized from acetic acid, m.p. 208°–209° C.

Analysis for: $C_{22}H_{17}NO_3S$: Calculated: C, 70.38; H, 4.56; N, 3.73. Found: C, 70.04; H, 4.56; N, 3.72.

EXAMPLE 13

4'-(Benzothiazolylmethoxy)-4-diphenyl-N-hydroxy-N-methyl-acetamide

A mixture of 4'-(benzothiazolylmethoxy)-4-diphenylacetic acid (1.0 g, 3.0 mmol), methylene chloride (50 ml) and dimethylacetamide (0.21 ml) is cooled to 5° C. and with stirring, a solution of oxalyl chloride (0.6 ml) in methylene chloride (10 ml) is added slowly. After stirring at room temperature for 30 minutes, the reaction mixture is poured into a solution containing tetrahydrofuran (13 ml), water (1.2 ml), triethylamine (2.0 ml) and N-methylhydroxylamine hydrochloride (1.0 g, 12.0 mmol). After stirring for 1 hour the reaction mixture is diluted with methylene chloride (100 ml), is poured into 2N hydrochloric acid (100 ml) and is extracted. The aqueous layer is washed again with methylene chloride (100 ml). The combined methylene chloride extract is washed with water (100 ml) and brine (100 ml), is dried over anhydrous magnesium sulfate and is concentrated under reduced pressure to afford 1.0 g of crude solid product. The solids are recrystallized from acetonitrile to give 0.6 g (60%) of a yellowish-colored crystalline solid, m.p. 176°–179° C.

Analysis for: $C_{23}H_{20}N_2O_3S$: Calculated: C, 68.30; H, 4.98; N, 6.93. Found: C, 68.70; H, 4.89; N, 6.62.

EXAMPLE 14

N-Hydroxy-4'-(2-benzothiazolylmethoxy)[1,1'-biphenyl]-4-acetamide

The title compound is prepared using the procedure of Example 13 employing the carboxylic acid from Example 12 and substituting hydroxylamine for N-methylhydroxylamine. Normal workup gives 1.0 g of crude solid. The solid is recrystallized from acetonitrile to give 0.60 g (60.0%) of crystalline product, m.p. 176°–179° C.

Analysis for: $C_{22}H_{18}N_2O_3S \cdot 0.5\ H_2O$: Calculated: C, 66.90; H, 4.72; N, 7.09. Found: C, 67.12; H, 4.68; N, 7.36.

EXAMPLE 15

N-Hydroxy-N-isopropyl-4'-(2-benzothiazolylmethoxy)[1,1'-biphenyl]-4-acetamide

The title compound is prepared using the procedure of Example 13 employing the carboxylic acid from Example 12 substituting N-isopropylhydroxylamine for N-methylhydroxylamine. Normal workup gives 0.6 g of crude solid. The solid is recrystallized from acetonitrile to give 0.20 g (14.2%) of beige crystalline product, m.p. 203°–204° C.

Analysis for: $C_{25}H_{24}N_2O_3S$: Calculated: C, 69.42; H, 5.59; N, 6.48. Found: C, 69.44; H, 5.52; N, 6.09.

EXAMPLE 16

N-Hydroxy-N,α-dimethyl-4′-(2-benzothiazolylmethoxy)[1,1′-biphenyl]-4-acetamide

A. α-Methyl-4′-(methoxy)[1,1′-biphenyl]-4-acetic acid, ethyl ester

The known starting material, 4′-methoxy-4-biphenylacetic acid (J. Chem. Soc. 1959, 557) is first converted to its ethyl ester by Fisher esterification with ethanol and concentrated sulfuric acid. To a solution of 4′-methoxy-4-biphenylacetic acid, ethyl ester (30.0 g, 0.110 mol) in tetrahydrofuran (400 mL) at −78° C. is added slowly, 2.01M lithium diisopropylamide (63 mL). The mixture is stirred for 30 minutes and then methyl iodide (30 mL) is added rapidly. The reaction mixture is warmed to 0° C. for 30 minutes, then at room temperature for 3 hours. The mixture is poured into water (2 L) and is extracted with ethyl acetate (3×1 L). The combined ethyl acetate extract is washed with 1N HCl (1 L), water (1 L) and brine (1 L), dried over MgSO4 and is concentrated under reduced pressure to give 48 g of crude yellow oil. Purification of the product by column chromatography (12% ethyl acetate in hexane) gives 22.0 g (69.6%) of crystalline material, m.p. 52°–54° C.

Analysis for: $C_{18}H_{20}O_3$: Calculated: C, 76.03; H, 7.09. Found: C, 76.33; H, 7.08.

B. α-Methyl-4′-(hydroxy)[1,1′-biphenyl]-4-acetic acid

A mixture containing α-methyl-4′-(methoxy)[1,1′-biphenyl]-4-acetic acid, ethyl ester (22.0 g, 77.4 mmol), acetic acid (400 mL) and 48% hydrobromic acid (80 mL) is refluxed for 18 hours. The solution is concentrated under reduced pressure to one-third the volume and the product crystallizes from the solution. The solid is filtered and dried to give a quantitative yield. A portion of this material is recrystallized from acetonitrile and a white solid is obtained, m.p. 205°–206° C. MS (EI m/z): 242 (M)+, (b.p., M-CO2H)+.

C. α-Methyl-4′-(hydroxy)[1,1′-biphenyl]-4-acetic acid, ethyl ester

A mixture of α-methyl-4′-(hydroxy)[1,1′-biphenyl]-4-acetic acid (22.0 g, 90.8 mmol) in ethanol (500 mL) and concentrated sulfuric acid (5.0 mL) is refluxed for 30 hours. The solution is concentrated under reduced pressure, is diluted with water (300 mL) and is extracted with ethyl acetate (3×300 mL). The combined ethyl acetate extract is washed with water (400 mL) and brine (400 mL), dried over MgSO4 and is concentrated under reduced pressure to give 20 g of crude product. Purification of this material by column chromatography (25% ethyl acetate in hexane) followed by crystallization from ethyl acetate and hexane gives 18.0 g (73.5%) of crystalline product, m.p. 124°–125° C., MS(CI+ m/z): 271[M+H]+.

Analysis for: $C_{17}H_{18}O_3$: Calculated: C, 75.53; H, 6.71. Found: C, 75.07; H, 6.66.

D. α-Methyl-4′-(2-benzothiazolylmethoxy)[1,1′-biphenyl]-4-acetic acid, ethyl ester The title compound is prepared using the procedure of Example 11B employing the above hydroxy-ester (5.0 g, 18.5 mmol). Normal workup gives a crude solid which is purified by column chromatography (30% ethyl acetate in hexane) to afford the desired product, 6.5 g (84.4%). A portion of the solid is recrystallized from ethyl acetate and hexane, m.p. 114°–115° C.

Analysis for: $C_{25}H_{23}NO_3S$: Calculated: C, 71.91; H, 5.55; N, 3.35. Found: C, 72.28; H, 5.54; N, 3.29.

E. α-Methyl-4′-(2-benzothiazolylmethoxy)[1,1′-biphenyl]-4-acetic acid

A solution of α-methyl-4′-(benzothiazolylmethoxy)-[1,1′-biphenyl]acetic acid, ethyl ester (6.0 g, 14.4 mmol), methanol (200 mL), tetrahydrofuran (200 mL) and 1N NaOH (25 mL) is refluxed for 18 hours. The reaction mixture is cooled to 0° C. and the product crystallizes from the solution. Filtration of the solid gives 4.0 g (67.8%) of product (m.p. greater than 250° C.). The α-methyl-4′-(benzothiazolylmethoxy)[1,1′-biphenyl]-4-acetic acid, sodium salt (3.8 g, 9.2 mmol) is dissolved in a mixture of tetrahydrofuran (250 mL) and methanol (250 mL) and 1N HCl (5.0 mL) is added. The solution is diluted with water (350 mL) and the product crystallizes from the reaction mixture. The solid is collected by filtration to afford the crude product. Recrystallization of the solid from acetonitrile gives 3.6 g (94.4%) of white crystalline product, m.p. 199°–200° C.

Analysis for: $C_{23}H_{19}NO_3S$: Calculated: C, 70.93; H, 4.92; N, 3.60. Found: C, 70.80; H, 4.81; N, 3.77.

F. N-Hydroxy-N,α-dimethyl-4′-(2-benzothiazolylmethoxy)[1,1′-biphenyl]-4-acetamide The title compound is prepared using the procedure of Example 13 employing the carboxylic acid from the previous step. Normal workup gives 2.0 g of crude solid. The solid is recrystallized from acetonitrile to give 1.6 g (76.2%) of crystalline product, m.p. 160°–161° C.

Analysis for: $C_{24}H_{22}N_2O_3S$: Calculated: C, 68.55; H, 5.75; N, 6.66. Found: C, 68.38; H, 5.41; N, 6.57.

EXAMPLE 17

N-Hydroxy-N,,a,-dimethyl-4′-(2-benzothiazolylmethoxy)[1,1′-biphenyl]-4-acetamide, sodium salt, methanol solvate A solution containing N-hydroxy-N,α,-dimethyl-4′-(2-benzothiazolylmethoxy)[1,1′-biphenyl]-4-acetamide (0.60 g, 1.43 mmol), in hot acetonitrile (150 mL) is treated with sodium methoxide (0.079 g, 1.43 mmol) in methanol (5 mL) and the product crystallizes from the solution. After storing the mixture overnight at 0° C., filtration of the white solid gives 0.59 g (93.7%) of product, (m.p. greater than 250° C.).

Analysis for: $C_{24}H_{21}N_2O_3SNa \cdot CH_3OH$: Calculated: C, 63.54; H, 5.33; N, 5.93. Found: C, 63.19; H, 5.24; N, 6.31.

EXAMPLE 18

N-Hydroxy-N-methyl-4′-[(2-phenylthiazol-4-yl)methoxy][1,1′-biphenyl]-4-acetamide A. 4′-[(2-Phenylthiazol-4-yl)methoxy][1,1′-biphenyl]-4-acetic acid, ethyl ester The title compound is prepared using the procedure of Example 11B employing the hydroxy-ester from Example 11A (6.0 g, 26.3 mmol) and substituting 4-(chloromethyl)-2-phenylthiazole for 2-(chloromethyl)-benzothiazole. Normal workup gives a crude solid which is purified by crystallization from hexane to afford 7.3 g (61.3%) of yellow colored product, m.p. 115°–117° C.

Analysis for: $C_{26}H_{23}NO_3S$: Calculated: C, 72.70; H, 5.40; N, 3.26. Found: C, 72.36; H, 5.39; N, 3.42.

B. 4'-[(2-Phenylthiazol-4-yl)methoxy][1,1'-biphenyl]-4-acetic acid

The title compound is prepared using the procedure of Example 16, part E employing the previous ester. The product crystallizes from the solution. The solid is collected by filtration to afford 4.2 g (88.6%) of product, m.p. 185°–189° C.

Analysis for: $C_{24}H_{19}NO_3S$: Calculated: C, 71.80; H, 4.77; N, 3.49. Found: C, 71.71; H, 4.80; N, 3.76.

C. N-Hydroxy-N-methyl-4'-[(2-phenylthiazol-4-yl)methoxy][1,1'-biphenyl]-4-acetamide The title compound is prepared using the procedure of Example 13 employing the previous acid. Normal workup affords 0.8 g of crude solid. The solid is recrystallized from acetonitrile to give 0.5 g (62.0%) of crystalline product, m.p. 159°–161° C.

Analysis for: $C_{25}H_{22}N_2O_3S$: Calculated: C, 69.75; H, 5.15; N, 6.51. Found: C, 69.49; H, 5.15; N, 6.29.

EXAMPLE 19

N-Hydroxy-N-methyl-4'-[(2-phenylthiazol-4-yl)methoxy][1,1'-biphenyl]-4-acetamide, sodium salt, sesquihydrate The title compound is prepared using the procedure of Example 17 employing the previous hydroxamic acid. The product crystallizes from the solution. After storing the mixture overnight at 0° C., filtration of the white solid gives 0.18 g (90.4%) of product, m.p. 230° C. (dec.).

Analysis for: $C_{24}H_{21}N_2O_3SNa.1.5\ H_2O$: Calculated: C, 62.60; H, 5.04; N, 5.83. Found: C, 62.54; H, 4.77; N, 5.50.

EXAMPLE 20

N-Hydroxy-N-isopropyl-4'-[(2-phenylthiazol-4-yl)methoxy][1,1'-biphenyl]-4-acetamide The title compound is prepared using the procedure of Example 13 employing the acid from Example 18 and substituting N-isopropylhydroxylamine for N-methylhydroxylamine. Normal workup gives 0.8 g of crude solid. The solid is recrystallized from acetonitrile to give 0.5 g (56.0%) of crystalline product, m.p. 174°–175° C.

Analysis for: $C_{25}H_{22}N_2O_3S$: Calculated: C, 70.72; H, 5.72; N, 6.11. Found: C, 70.90; H, 5.80; N, 6.03.

EXAMPLE 21

N-Hydroxy-N,α-dimethyl-4'-[(2-phenylthiazol-4-yl)methoxy][1,1'-biphenyl]-4-acetamide A. α-Methyl-4'-[(2-phenylthiazol-4-yl)methoxy][1,1'-biphenyl]-4-acetic acid, ethyl ester The title compound is prepared using the procedure of Example 11B employing the hydroxy-ester from part C of Example 16 and substituting 4-(chloromethyl)-2-phenylthiazole for 2-(chloromethyl)benzothiazole. Normal workup gives 8.0 g of a crude solid which is purified by column chromatography (30% ethyl acetate in hexane), affording 6.5 g (79.3%) of white crystalline product, m.p. 85°–86° C.

Analysis for: $C_{27}H_{25}NO_3S$: Calculated: C, 73.11; H, 5.68; N, 3.16. Found: C, 72.86; H, 5.67; N, 2.93.

B. α-Methyl-4'-[(2-phenylthiazol-4-yl)methoxy][1,1'-biphenyl]-4-acetic acid

The title compound is prepared using the procedure of part E of Example 16 employing the above ester. The product crystallizes from the solution. The solid is collected by filtration to afford 4.2 g (83.0%) of product, m.p. 203°–204° C.

Analysis for: $C_{25}H_{21}NO_3S$: Calculated: C, 72.27; H, 5.09; N, 3.37. Found: C, 72.03; H, 4.95; N, 3.41.

C. N-Hydroxy-N,α-dimethyl-4'-[(2-phenylthiazol-4-yl)methoxy]-[1,1'-biphenyl]4-acetamide The title compound is prepared using the procedure of Example 13 employing the previously prepared acid. Normal workup gives 2.0 g of crude solid. The solid is recrystallized from acetonitrile to give 1.6 g (76.2%) of crystalline product, m.p. 180°–181° C.

Analysis for: $C_{26}H_{24}N_2O_3S$: Calculated: C, 70.25; H, 5.44; N, 6.30. Found: C, 69.91; H, 5.35; N, 6.19.

EXAMPLE 22

N-Hydroxy-N,α-dimethyl-4'-[(2-phenylthiazol-4-yl)methoxy][1,1'-biphenyl]-4-acetamide, sodium salt, hydrate The title compound is prepared using the procedure of Example 17 employing the previously synthesized hydroxamic acid. After storing the mixture overnight at 0° C., filtration of the white solid gives 0.61 g (82.8%) of product, m.p. 166° C. (dec.).

Analysis for: $C_{26}H_{23}N_2O_3SNa.1\ H_2O$: Calculated: C, 64.44; H, 5.20; N, 5.78. Found: C, 64.79; H, 5.10; N, 6.32.

EXAMPLE 23

N-Hydroxy-N,α-dimethyl-4'-[(1-methyl-1H-benzimidazol-2-yl)methoxy]-[1,1'-biphenyl]-4-acetamide A. α-Methyl-4'-[(1-methyl-1H-benzimidazol-2-yl)[methoxy][1,1'-biphenyl]-4-acetic acid, ethyl ester, quarter hydrate The title compound is prepared using the procedure of Example 11B employing the hydroxy-ester from part C of Example 16 and substituting N-methyl-2-(chloromethyl)benzimidazole for 2-(chloromethyl)benzothiazole. Normal workup gives 8.0 g of crude solid which is purified by column chromatography (65% ethyl acetate in hexane) to afford 5.1 g (66.5%) of product. A portion of this material is recrystallized from ethyl acetate to give white crystalline solid, m.p. 136°–138° C., MS(EI+ m/z): 414 (m)+.

Analysis for: $C_{26}H_{26}N_2O_3.0.25\ H_2O$: Calculated: C, 74.53; H, 6.37; N, 6.68. Found: C, 74.53; H, 6.23; N, 6.64.

B. α-Methyl-4'-[(1-methyl-1H-benzimidazol-2-yl)methoxy][1,1'-biphenyl]-4-acetic acid hydrate The title compound is prepared using the procedure of part E of Example 16 employing the above ester. The precipitated solid is collected by filtration to afford 2.0 g (48%) of product. A portion of this material is recrystallized from acetonitrile to give purified crystals, m.p. 228°–230° C.

Analysis for: $C_{24}H_{22}N_2O_3.H_2O$: Calculated: C, 71.27; H, 5.98; N, 6.92. Found: C, 71.59; H, 5.60; N, 7.17.

C. N-Hydroxy-N,α-dimethyl-4'-[(1-methyl-1H-benzimidazol-2-yl)methoxy][1,1'-biphenyl]-4-acetamide The title compound is prepared using the procedure of Example 13 employing the previously prepared acid. Normal workup affords 2.2 g of crude solid which is recrystallized from acetonitrile to give 1.3 g (59.0%) of crystalline product, m.p. 195°–197° C.

Analysis for: $C_{25}H_{25}N_3O_3$: Calculated: C, 72.27; H, 6.06; N, 10.11. Found: C, 72.15; H, 6.02; N, 10.60.

EXAMPLE 24

N-Hydroxy-N,α-dimethyl-4'-[(1-methyl-1H-benzimidazol-2-yl)methoxy]-[1,1'-biphenyl]-4-acetamide, hydrochloride salt A solution containing N-hydroxy-N,α-dimethyl-4'-[(1-methyl-1H-benzimidazol-2-yl)methoxy]-[1,1'-biphenyl]-4-acetamide (0.2 g, 0.48 mmol) in warm methanol (100 mL) is treated with 1M hydrogen chloride in diethyl ether (3 mL). The solution is concentrated under reduced pressure to a solid residue. This material is crystallized from a mixture of ethanol and diethyl ether to give 0.2 g (92.2%) of white crystalline product, m.p. 131° C. (dec.).

Analysis for: $C_{25}H_{25}N_3O_3 \cdot HCl$: Calculated: C, 66.44; H, 5.80; N, 9.30. Found: C, 66.06; H, 6.14; N, 8.95.

EXAMPLE 25

N-Hydroxy-N-methyl-2-phenyl-α-[4'-[(2-phenylthiazol-4-yl)methoxy]-[1,1'-biphenyl]-4-yl]-thiazolepropanamide A. 4'-[(2-Phenylthiazol-4-yl)methoxy]-α-[(2-phenylthiazol-4-yl)methyl][1,1'-biphenyl]-4-acetic acid, ethyl ester A slurry of the hydroxy-ester (6.9 g, 30.2 mmol) from Example 11A and cesium carbonate (15.0 g, 46.0 mmol) in dimethylsulfoxide (150 mL) is stirred at room temperature. After 30 minutes, 4-(chloromethyl)-2-phenylthiazole (12.6 g, 60.2 mmol) is added and the mixture is stirred for 18 hours. The reaction mixture is poured into water (800 mL) and extracted with ethyl acetate (3×500 mL). The combined ethyl acetate extract is washed with water (300 mL), brine (300 mL), dried over $MgSO_4$, and concentrated under reduced pressure to give 10.0 g of a crude solid. A 5 g portion of this material is purified by column chromatography (0.1% methanol in methylene chloride) followed by crystallization from ethyl acetate and hexane to afford 2.0 g of white crystalline product, m.p. 85°-87° C.

Analysis for: $C_{36}H_{30}N_2O_3S_2$ Calculated: C, 71.73; H, 5.02; N, 4.65. Found: C, 71.67; H, 5.13; N, 4.98.

B. 4'-[(2-Phenylthiazol-4-yl)methoxy]-α-[(2-phenylthiazol-4-yl)methyl][1,1'-biphenyl]-4-acetic acid The title compound is prepared using the procedure of part E of Example 16 employing the above ester. Normal workup affords a crude solid which is crystallized from acetic acid to afford 1.2 g (78.9%) of product, m.p. 195°-197° C.

Analysis for: $C_{34}H_{26}N_2O_3S_2$: Calculated: C,71.06; H,4.56; N,4.87. Found: C,71.04; H,4.67; N,4.93.

C. N-Hydroxy-N-methyl-2-phenyl-α-[4'-[(2-phenylthiazol-4-yl)methoxy]-[1,1'-biphenyl]-4-yl]-thiazolepropanamide The title compound is prepared using the procedure of Example 13 employing the previously prepared acid. Normal workup affords 0.6 g (75.0%) of product, m. p. 60°-75° C.

Analysis for: $C_{35}H_{29}N_3O_3S_2 \cdot H_2O$: Calculated: C,67.66; H,5.03; N,6.76. Found: C,67.69; H,4.96; N,6.64.

EXAMPLE 26

4'-(Benzothiazolylmethoxy)-2-fluoro-N-hydroxy-N-methyl-[1,1'-biphenyl]-4-acetamide A. 4'-(Benzothiazolylmethoxy)-2-fluoro[1,1'-biphenyl]-4-acetic acid methyl ester 0.1 hydrate The title compound is prepared using the method of Example 2F substituting 2-(chloromethyl)benzothiazole for 2-(chloromethyl)quinoline. Normal workup followed by recrystallization from methanol affords 1.2 g (67%) of white crystals, m.p. 116°-118° C.

Analysis for: $C_{23}H_{18}NO_3FS \cdot 0.1\ H_2O$: Calculated: C, 67.50; H, 4.48; N, 3.42. Found: C, 67.24; H, 4.70; N, 3.52.

B. 4'-(Benzothiazolylmethoxy)-2-fluoro[1,1'-biphenyl]-4-acetic acid

The title compound is prepared using the method of Example 2G employing the above ester. Normal workup affords 0.87 g (70%) of white crystals, m.p. 171°-173° C.

Analysis for: $C_{22}H_{16}NO_3FS$: Calculated: C, 67.16; H, 4.10; N, 3.56. Found: C, 67.23; H, 4.25; N, 3.55.

C. 4'-(Benzothiazolylmethoxy)-2-fluoro-N-hydroxy-N-methyl-[1,1'-biphenyl]-4-acetamide The title compound is prepared using the methods of Example 8 employing the above carboxylic acid and omitting the dimethylformamide and aqueous tetrahydrofuran. Quenching the reaction by addition of water affords 0.35 g (46%) of a white solid, m.p. 178°-180° C.

Analysis for: $C_{23}H_{19}N_2O_3FS$: Calculated: C, 65.39; H, 4.53; N, 6.63. Found: C, 65.58; H, 4.47; N, 6.57.

EXAMPLE 27

2-Fluoro-N-hydroxy-N-methyl-4'-[2-phenyl-4-thiazolyl)methoxy]-[1,1'-biphenyl]-4-acetamide A. 2-Fluoro-4'-[2-phenyl-4-thiazolyl)methoxy]-[1,1'-biphenyl]-4-acetic acid methyl ester The title compound is prepared using the method of Example 2F substituting 4-(chloromethyl)-2-phenylthiazole for 2-(chloromethyl)quinoline. Normal workup followed by flash chromatography, eluting with 7:3 ethyl acetate-hexane), affords 0.69 g (27%) of white crystals, m.p. 87°-88° C.

Analysis for: $C_{25}H_{20}NO_3FS$: Calculated: C, 69.27; H, 4.65; N, 3.23. Found: C, 69.03; H, 4.73; N, 2.99.

B. 2-Fluoro-4'-[2-phenyl-4-thiazolyl)methoxy]-[1,1'-biphenyl]-4-acetic acid

The title compound is prepared using the method of Example 2G employing the above ester. Normal workup affords 3.6 g (93%) of white crystals, m.p. 155°-158° C.

Analysis for: $C_{24}H_{18}NO_3FS$: Calculated: C, 68.72; H, 4.33; N, 3.34. Found: C, 68.85; H, 4.29; N, 2.94.

C. 2-Fluoro-N-hydroxy-N-methyl-4'-[2-phenyl-4-thiazolyl)methoxy]-[1,1'-biphenyl]-4-acetamide The title compound is prepared using the method of Example 8 employing the above carboxylic acid. Normal workup followed by trituration with ethyl acetate-hexane affords 0.37 g (11%) of a white solid, m.p. 116°-119° C.

Analysis for: $C_{25}H_{21}N_2O_3FS$: Calculated: C, 66.95; H, 4.72; N, 6.25. Found: C, 66.30; H, 4.85; N, 6.25.

EXAMPLE 28

2-Fluoro-N-hydroxy-N-methyl-4'-(2-pyridinylmethoxy)-[1,1'-biphenyl]-4-acetamide

A. 2-Fluoro-N-hydroxy-N-methyl-4'-(2-pyridinylmethoxy)-[1,1'-biphenyl]-4-acetic acid The title compound is prepared using the methods of Examples 2F and G substituting 2-(chloromethyl)pyridine for 2-(chloromethyl)quinoline. Normal workup of the ester followed by flash chromatography, eluting with 1:1 ethyl acetatehexane, affords 1.1 g (29%) of the ester which is subsequently hydrolyzed to afford 0.94 g (89%) of the title compound as a white solid, m.p. 166°-169° C.

Analysis for: $C_{20}H_{16}NO_3F$: Calculated: C, 71.21; H, 4.78; N, 4.15. Found: C, 71.28; H, 4.74; N, 3.96.

B. 2-Fluoro-N-hydroxy-N-methyl-4'-(2-pyridinylmethoxy)-[1,1'-biphenyl]-4-acetamide The title compound is prepared using the method of Example 8 employing the above carboxylic acid. Normal workup followed by flash chromatography, eluting with 6:4 ethyl acetate-hexane, and recrystallization from ethyl acetate-hexane affords 0.07 g (10%) of a white solid, m.p. 137°–139° C.

Analysis for: $C_{21}H_{19}N_2O_3F$: Calculated: C, 68.84; H, 5.23; N, 7.65. Found: C, 68.74; H, 5.60; N, 6.75.

EXAMPLE 29

2-[2-Fluoro-4'-(1-methyl-1H-benzimidazol-2-ylmethoxy)biphenyl-4-yl]-N-hydroxy-N-methyl-4-acetamide A. 2-[2-Fluoro-4'-(1-methyl-1H-benzimidazol-2-ylmethoxy)-biphenyl-4-yl]-4-acetic acid The title compound is prepared using the methods of Example 2F and G substituting 2-(chloromethyl)1-methyl-1H-benzoimidazole for 2-(chloromethyl)quinoline. Normal workup followed by recrystallization from ethyl acetate affords white crystals, m.p. 224°–226° C.

Analysis for: $C_{23}H_{19}N_2O_3F$: Calculated: C, 70.76; H, 4.91; N, 7.48. Found: C, 70.93; H, 4.89; N, 7.49.

B. 2-[2-Fluoro-4'-(1-methyl-1H-benzimidazol-2-ylmethoxy)-biphenyl-4-yl]-N-hydroxy-N-methyl-4-acetamide The title compound is prepared using the method of Example 8. Normal workup followed by flash chromatography, eluting with 6:4 ethyl acetate-hexane, affords 0.1 g (10%) of a white solid, m.p. 203°–205° C.

Analysis for: $C_{24}H_{22}N_3O_3F$: Calculated: C, 68.72; H, 5.29; N, 10.02. Found: C, 68.37; H, 5.35; N, 9.78.

EXAMPLE 30

2-{3-[4-(Benzothiazol-2-ylmethoxy)-benzoyl]-phenyl}-N-hydroxy-N-methyl-4-acetamide 0.6 ethyl acetate solvate A. 2-{3-[4-(Benzothiazol-2-ylmethoxy)-benzoyl]-phenyl}-4-acetic acid methyl ester The title compound is prepared using the method of Example 3G substituting 2-(chloromethyl)benzothiazole for 2-(chloromethyl)quinoline. Normal workup followed by recrystallization from ethyl acetate-hexane affords 3.3 g (53%) of the title compound.

B. 2-{3-[4-(Benzothiazol-2-ylmethoxy)-benzoyl]-phenyl}-4-acetic acid

The title compound is prepared using the method of Example 3H employing the above ester. Normal workup affords 2.5 g (79%) of the acid as a white solid.

C. 2-{3-[4-(Benzothiazol-2-ylmethoxy)-benzoyl]-phenyl}-N-hydroxy-N-methyl-4-acetamide 0.6 ethyl acetate solvate The title compound is prepared using the method of Example 8 employing the above carboxylic acid and using carbonyldiimidazole in place of oxalyl chloride and omitting the dimethylformamide. Quenching the reaction by addition of water followed by flash chromatography, eluting with 5:2:2.5:0.5 methylene chloride-ethyl acetate-hexane-ethanol, affords the title compound as a white solid, m.p. 149°–151° C.

Analysis for: $C_{24}H_{20}N_2O_4S.0.6\ C_4H_8O_2$: Calculated: C, 65.33; H, 5.10; N, 5.77. Found: C, 65.03; H, 4.76; N, 6.13.

EXAMPLE 31

4-{4-[(1-Methyl-1H-benzimidazol-2-yl)methoxy]-phenyl}-5-phenyl-2-oxazole N-hydroxy-N-methyl propanamide, hydrate 0.5 ethyl acetate solvate The title compound is prepared using the method of part C of Example 30 and employing the acid from Example 7. Normal workup affords white crystals, m.p. 148°–152° C.

Analysis for: $C_{28}H_{26}N_4O_4.0.5\ C_4H_8O_2.H_2O$: Calculated: C, 66.17; H, 5.92; N, 10.28. Found: C, 65.91; H, 5.28; N, 11.10.

EXAMPLE 32

4-{4-[(benzothiazol-2-yl)methoxy]-phenyl}-5-phenyl-2-oxazole N-hydroxy-N-methyl propanamide The acid, 4-{4-[(benzothiazol-2-yl)methoxy]-phenyl}-5-phenyl-2-oxazole N-hydroxy-N-methyl propanoic acid, is first prepared using the method of Example 7 substituting 2-(chloromethyl)benzothiazole for N-methyl-2-(chloromethyl)benzimidazole. The title compound is prepared using the method of part C of Example 30 and employing the previously prepared acid. Normal workup affords white crystals, m.p. 152°–155° C.

Analysis for: $C_{27}H_{23}N_3O_4S$: Calculated: C, 66.79; H, 4.77; N, 8.65. Found: C, 66.59; H, 4.68; N, 8.48.

EXAMPLE 33

1-{1-[4'-(Benzothiazol-2-ylmethoxy)biphenyl-4-yl]-ethyl}-1-hydroxy-urea

A. 4-Acetoxy-4'-hydroxy-1,1'-biphenyl

The title compound is prepared using the method of part B of Example 16 substituting 4-acetoxy-4'-methoxy-1,1'-biphenyl for α-methyl-4'-(methoxy)[1,1'-biphenyl]-4-acetic acid, ethyl ester. Normal workup affords a white solid, m.p. 204°–207° C.; MS (EI m/z): 212 (M)+, 197 (b.p.,M—CH3)+.

B. 4-(α-Hydroxyethyl)-4'-hydroxy-1,1'-biphenyl

A solution containing 4-acetoxy-4'-hydroxy-1,1'-biphenyl from part A (5.0 g, 23.6 mmol) in methanol (500 mL) and tetrahydrofuran (30 mL) is treated with sodium borohydride (0.9 g, 23.8 mmol) in portions over 30 minutes at room temperature. After 2 hours, the reaction mixture is concentrated under reduced pressure, diluted with water (400 mL), acidified with 2N HCl and extracted with ethyl acetate. The organic layer is washed with water and brine, dried over MgSO4 and concentrated to a solid residue. Crystallization of the solid from ethyl acetate gives 4.7 g (92.9%) of the title compound, m.p. 159°–160° C.; MS (EI m/z): 214 (M)+ and 199 (b.p. M—CH3)+.

C. 4-(α-Hydroxyethyl)-4'-(benzothiazol-2-ylmethoxy)-1,1'-biphenyl

The title compound is prepared using the method of Example 11B employing the above phenol. Normal workup gives 1.3 g (86.7%) of crystalline product, m.p. 205°–206° C.

Analysis for: $C_{22}H_{19}NO_2S$: Calculated: C, 73.10; H, 5.30; N, 3.88. Found: C, 73.29; H, 5.27; N, 3.85.

D. N,O-Bis(tert-butoxycarbonyl)-1-{1-[4-(benzothiazol-2-ylmethoxy)-biphenyl-4-yl]-ethyl}-1-hydroxylamine To a mixture containing 4-(a-hydroxyethyl)-4'-(benzothiazol-2-ylmethoxy)-1,1'-biphenyl from Part C (4.0 g, 11.1 mmol), triphenylphosphine (5.0 g, 22.0 mmol)

and N,O-bis(tert-butoxycarbonyl)hydroxylamine (5.13 g, 22.0 mmol) in tetrahydrofuran (160 mL) is added a solution of diethyl azodicarboxylate (1.5 mL, 11.1 mmol) in tetrahydrofuran (80 mL) over 30 minutes. The reaction mixture is stirred overnight, concentrated to a volume of 50 mL and upon cooling at −10° C., the product crystallizes to give 4.0 g of crude material. Purification of the solid by chromatography (30% ethyl acetate in hexane) yields 3.1 g (48.4%) of the title compound, m.p. 139°–143° C.; MS (EI m/z): 376M)+.

E. 1-{1-[4-(Benzothiazol-2-ylmethoxy)-biphenyl-4-yl]-ethyl}-1-hydroxylamine

A solution of N,O-bis(tert-butoxycarbonyl)-1-{1-[4-(benzothiazol-2-ylmethoxy)-biphenyl-4-yl]-ethyl}-1-hydroxylamine from Part D (0.11 g, 0.19 mmol) in trifluoroacetic acid (3 mL) is stirred at room temperature for 30 minutes. The solution is poured into 0.5N NaOH (100 mL) and the product crystallizes from the solution to give 0.85 g of a crude solid. Crystallization of the solid from ethyl acetate and hexane gives 0.050 g (69.5%) of white solid material, m.p. 176°–180° C. (dec.); MS (EI m/z): 376(M)+ and 344 (b.p., M-NHOH)+.

F. 1-{1-[4-(Benzothiazol-2-ylmethoxy)-biphenyl-4-yl]-ethyl}-1-hydroxy-urea

A solution of 1-{1-[4-(benzothiazol-2-ylmethoxy)-biphenyl-4-yl]-ethyl}-1-hydroxylamine from Part E (0.7 g, 1.86 mmol) and trimethylsilylisocyanate (1.5 mL, 11.08 mmol) in dioxane (100 mL) is stirred for 24 hours. The mixture is poured into saturated NH$_4$Cl and the product crystallizes to give 0.7 g of a crude solid. Purification of this material by chromatography (THF) and trituration from diethyl ether yields 0.35 g of the title compound, m.p. 190°–191° C.; MS(CI m/z): 420 (M+H)+.

EXAMPLE 34

N-{1-[4'-(Benzothiazol-2-ylmethoxy)-biphenyl-4-yl]-ethyl}-N-hydroxy-acetamide

A. O-Acetoxy-N-{1-[4'-(benzothiazol-2-ylmethoxy)-biphenyl-4-yl]-ethyl}-N-hydroxy-acetamide To a solution of the hydroxylamine from part E of Example 33 (0.75 g, 1.99 mmol) and triethylamine (0.61 g, 6.0 mmol) in methylene chloride (180 mL) and tetrahydrofuran (5 mL) is added slowly acetyl chloride (0.43 g, 6.0 mmol). After 1 hour, the mixture is poured into 2N HCl (200 mL) and extracted. The methylene chloride layer is washed with water, brine, dried over MgSO$_4$ and concentrated to give 0.53 g of a crude solid. Purification of the solid by chromatography (1:1 ethyl acetate:hexane) gives 0.37 g (40.2%) of white crystalline title compound, m.p. 168°–174° C.

Analysis for: C$_{22}$H$_{24}$N$_2$O$_4$S: Calculated: C, 67.81; H, 5.25; N, 6.08. Found: C, 67.63; H, 5.23; N, 6.04.

B. N-{1-[4'-(Benzothiazol-2-ylmethoxy)-biphenyl-4-yl]-ethyl}-N-hydroxy-acetamide To a solution of O-acetoxy-N-{1-[4'-(benzothiazol-2-ylmethoxy)-biphenyl-4-yl]-ethyl}-1-hydroxy-acetamide (0.30 g, 0.652 mmol) in isopropyl alcohol (70 mL) and THF (15 mL) is added dropwise a solution of LiOH (0.14 g, 3.26 mmol) in water (3 mL). After 30 minutes, the reaction mixture is neutralized with 2N HCl and concentrated under reduced pressure. To the residue is added ethyl acetate and water and the mixture is extracted. The organic layer is washed with water, brine, dried over MgSO$_4$ and concentrated to give 0.25 g of a crude solid. Crystallization of the solid from ethyl acetate yields 0.21 g (77.0%) of title compound as a white crystalline material, m.p. 197°–199° C.

Analysis for: C$_{24}$H$_{22}$N$_2$O$_3$S: Calculated: C, 68.88; H, 5.30; N, 6.69. Found: C, 69.07; H, 5.30; N, 6.56.

EXAMPLE 35

1-{1-[4'-(Benzoxazol-2-ylmethoxy)-biphenyl-4-yl]-ethyl}-1-hydroxy-urea

A. 4-(α-Hydroxyethyl)-4'-(benzoxazol-2-ylmethoxy)-1,1'-biphenyl

The title compound is prepared using the method of Example 11B employing the phenol from part B of Example 33 and substituting 2-(chloromethyl)benzoxazole for 2-(chloromethyl)benzothiazole. Normal workup gives 8.0 g (70.8%) of title compound as a crystalline product, m.p. 166°–169° C.

Analysis for: C$_{22}$H$_{19}$NO$_3$: Calculated: C, 76.50; H, 5.54; N, 4.06. Found: C, 76.88; H, 5.76; N, 4.06.

B. N,O-Bis(tert-butoxycarbonyl)-1-{1-[4-(benzoxazol-2-ylmethoxy)-biphenyl-4-yl]-ethyl}-1-hydroxylamine The title compound is prepared using the method of part D. of Example 33 and employing the compound from Part A. Normal workup yields 3.1 g (53.2%) of the title compound, m.p. 127°–132° C.; MS (CI m/z): 561 (M+H)+.

Analysis for: C$_{32}$H$_{36}$N$_2$O$_7$: Calculated: C, 68.56; H, 6.47; N, 5.00. Found: C, 68.95; H, 6.48; N, 4.72.

C. 1-{1-[4-(Benzoxazol-2-ylmethoxy)-biphenyl-4-yl]-ethyl}-1-hydroxylamine

The title compound is prepared using the method of part E. of Example 33 and employing the compound from Part B. Normal workup gives 2.7 g (71.7%) of the title compound as a white solid; MS (EI m/z): 360 (M)+ and 328 (b.p., M-NHOH)+.

Analysis for: C$_{22}$H$_{20}$N$_2$O$_3$ Calculated: C, 73.32; H, 5.59; N, 7.77.

Found: C, 73.13; H, 5.59; N, 7.93.

D. 1-{1-[4-(Benzoxazol-2-ylmethoxy)-biphenyl-4-yl]-ethyl}-1-hydroxy-urea

The title compound is prepared using the method of part F. of Example 33 and employing the compound from Part C. Normal workup gives 0.7 g of the title compound as white crystals, m.p. 167°–168° C.(dec.); MS (CI M/Z): 404 (M+H)+.

EXAMPLE 36

N-{1-[4'-(Benzoxazol-2-ylmethoxy)-biphenyl-4-yl]-ethyl}-N-hydroxy-acetamide

A. O-Acetoxy-N-{1-[4'-(benzoxazol-2-ylmethoxy)-biphenyl-4-yl]-ethyl}-N-hydroxy-acetamide The title compound is prepared using the method of part A. of Example 34 using the hydroxylamine from part C of Example 35. Normal workup gives 1.6 g (99.0%) of the title compound as a white solid, m.p. 98.0°–100.0° C.

Analysis for: C$_{26}$H$_{24}$N$_2$O$_5$: Calculated: C, 70.26; H, 5.44; N, 6.30. Found: C, 70.27; H, 5.52; N, 6.16.

B. N-{1-[4'-(Benzoxazol-2-ylmethoxy)-biphenyl-4-yl]-ethyl}-N-hydroxy-acetamide

The title compound is prepared using the method of part B. of Example 34 and employing the compound of Part A. Normal workup gives 1.0 g (71.4%) of the title compound as a white crystalline material, m.p. 171°–172° C.

Analysis for: C$_{24}$H$_{22}$N$_2$O$_4$: Calculated: C, 71.63; H, 5.51; N, 6.96. Found: C, 71.56; H, 5.55; N, 6.88.

EXAMPLE 37

N-Hydroxy-N-{1-[4'-(1-methyl-1H-benzimidazol-2-ylmethoxy)-biphenyl-4-yl]-ethyl}-1-acetamide A. 4-(α-Hydroxyethyl)-4'-(1-methyl-1H-benzimidazol-2-ylmethoxy)-1,1'-biphenyl The title compound is prepared using the method of Example 11B employing the phenol from part C of Example 33 and substituting 2-(chloromethyl)-1-methylbenzimidazole for 2-(chloromethyl)benzthiazole. Normal workup gives 7.0 g (59.7%) of the title compound as a crystalline product, m.p. 216°-219° C.

Analysis for: $C_{23}H_{22}N_2O_2$: Calculated: C, 77.07; H, 6.19; N, 7.82. Found: C, 77.41; H, 6.19; N, 7.69.

B. N,O-Bis(tert-butoxycarbonyl)-1-{1-[4-(1-methyl-1H-benzimidazol-2-ylmethoxy)-biphenyl-4-yl]-ethyl}-1-hydroxylamine The title compound is prepared using the method of part D. of Example 33 and employing the compound from Part A. Normal workup gives 9.2 g (82.0%) of the title compound.

C. 1-{1-[4-(1-Methyl-1H-benzimidazol-2-ylmethoxy)-biphenyl-4-yl]-1-hydroxylamine.TFA salt The title compound is prepared using the method of part E. of Example WAY-33 and employing the compound from Part B. Normal workup gives 3.1 g (55.4%) of the title compound as a white solid, m.p. 185°-187° C. (dec.); MS (CI m/z): 374 (M+H−TFA)+.

D. O-Acetoxy-N-{1-[4'-(1-methyl-1H-benzimidazol-2-ylmethoxy)-biphenyl-4-yl]-ethyl}-N-hydroxy-acetamide The title compound is prepared using the method of part A. of Example 34 and employing the compound from Part C. Normal workup gives 0.65 g (35.5%) of the title compound as a white solid, m.p. 163°-169° C.; MS (CI m/z): 458 (M+H)+.

E. N-Hydroxy-N-{1-[4'-(1-methyl-1H-benzimidazol-2-ylmethoxy)-biphenyl-4-yl]-ethyl}-acetamide The title compound is prepared using the method of part B. of Example 34 employing the compound from Part D. Normal workup gives 0.3 g (55.6%) of title compound as a white crystalline material, m.p. 211°-213° C. (decomposed).

Analysis for: $C_{25}H_{25}N_3O_3$ Calculated: C, 72.27; H, 6.07; N, 10.11. Found: C, 72.10; H, 6.11; N, 9.93.

EXAMPLE 38

1-{1-[4'-(2-Phenylthiazol-4-ylmethoxy)-biphenyl-4-yl]-ethyl}-1-hydroxy-urea

A. 4-(α-Hydroxyethyl)-4'-(2-phenylthiazol-4-ylmethoxy)-1,1'-biphenyl

The title compound is prepared using the method of Example 11B employing the phenol from part C of Example 33 and substituting 4-chloromethyl-2-phenylthiazole for 2-(chloromethyl)benzthiazole. Normal workup gives 9.8 g (77.2%) of the title compound as a crystalline product, m.p. 164°-165° C.

Analysis for: $C_{24}H_{21}NO_2S$: Calculated: C, 74.39; H, 5.46; N, 3.61. Found: C, 74.11; H, 5.43; N, 3.53.

B. N,O-Bis(tert-butoxycarbonyl)-1-{1-[4-(2-phenylthiazol-4-ylmethoxy)-biphenyl-4-yl]-ethyl}-1-hydroxylamine The title compound is prepared using the method of part D. of Example 33 and employing the compound from Part A. Normal workup gives 8.0 g (54.1%) of the title compound as white crystals, m.p. 128°-129° C.

Analysis for: $C_{34}H_{38}N_2O_6S$: Calculated: C, 67.75; H, 6.35; N, 4.65. Found: C, 67.66; H, 6.33; N, 4.68.

C. 1-{1-[4-(2-Phenylthiazol-4-ylmethoxy)-biphenyl-4-yl]-ethyl}-1-hydroxylamine

The title compound is prepared using the method of part E. of Example 33 and employing the compound from Part B. Normal workup gives 3.2 g (43.0%) of the title compound as a white solid, MS (EI m/z): (M)+.

Analysis for: $C_{24}H_{22}N_2O_2S$: Calculated: C, 71.62; H, 5.51; N, 6.96. Found: C, 71.23; H, 5.62; N, 6.57.

D. 1-{1-[4-(2-Phenylthiazol-4-ylmethoxy)-biphenyl-4-yl]-ethyl}-1-hydroxy-urea

The title compound is prepared using the method of part F of Example 33 and employing the compound from Part C. Normal workup gives 0.75 g (56.1%) of the title compound, m.p. 175°-176° C. (decomposed); MS ((+)FAB m/z): 446 (M+H)+.

EXAMPLE 39

N-{1-[4'-(2-Phenylthiazol-4-ylmethoxy)-biphenyl-4-yl]-ethyl}-N-hydroxy-acetamide A. O-Acetoxy-N-{1-[4'-(2-Phenylthiazol-4-ylmethoxy)-biphenyl-4-yl]-ethyl}-N-hydroxy-acetamide The title compound is prepared using the method of part A. of Example 34 and employing the compound from Part C of Example 38. Normal workup gives 1.6 g (78.4%) of the title compound as a white solid, m.p. 95°-96° C.; MS (CI m/z): 487 (M+H)+.

Analysis for: $C_{28}H_{26}N_2O_4S$: Calculated: C, 69.12; H, 5.39; N, 5.76. Found: C, 68.88; H, 5.43; N, 5.57.

B. N-{1-[4'-(2-Phenylthiazol-4-ylmethoxy)-biphenyl-4-yl]-ethyl}-N-hydroxy-acetamide The title compound is prepared using the method of part B. of Example 34 and employing the compound from Part A. Normal workup gives 1.1 g (78.0%) of the title compound as a white crystalline material, m.p. 183°-184.5° C.; MS (CI m/z): 445 (M+H)+.

Analysis for: $C_{26}H_{24}N_2O_3S$: Calculated: C, 70.25; H, 5.44; N, 6.30. Found: C, 70.07; H, 5.52; N, 6.25.

EXAMPLE 40

1-{1-[4'-(Benzothiazol-2-ylmethoxy)-2-fluoro-(1,1'-biphenyl)-4-yl]-ethyl}-1-hydroxy-urea A. 1-[4'-(Benzothiazol-2-ylmethoxy)-2-fluoro-(1,1'-biphenyl)-4-yl]-ethanone The methoxy compound from part B of Example 2 is first converted to the corresponding hydroxy compound by refluxing in 48% HBr in acetic acid. The title compound is prepared using the method of part B of Example 11 employing the previously synthesized hydroxy-ketone. Normal workup affords a white solid, m.p. 170°-172° C.

Analysis for: $C_{22}H_{16}NO_2SF$: Calculated: C, 70.01; H, 4.27; N, 3.71. Found: C, 69.47; H, 4.27; N, 3.88.

B. 1-[4'-(Benzothiazol-2-ylmethoxy)-2-fluoro-(1,1'-biphenyl)-4-yl]-ethanol

The title compound is prepared using the method of part B of Example 33 but substituting LiAlH4 for sodium borohydride and employing the compound from Part A. Normal workup followed by flash chromatography (eluant:hexane-ethyl acetate 6:4) affords the title compound.

C. 1-{1-[4'-(Benzothiazol-2-ylmethoxy)-2-fluoro-(1,1'-biphenyl)-4-yl]-ethyl}-1-hydroxylamine The title compound is prepared using the method of parts D and E of Example 33 employing the above alcohol. Normal workup gives a white solid.

D. 1-{1-[4'-(Benzothiazol-2-ylmethoxy)-2-fluoro-(1,1'-biphenyl)-4-yl]-ethyl}-1-hydroxy-urea The title compound is prepared using the method of part F of Example 33 employing the above hydroxylamine. Normal workup gives a white solid, m.p. 185°-186° C.

Analysis for: $C_{23}H_{20}N_3O_3SF$: Calculated: C, 63.14; H, 4.61; N, 9.60. Found: C, 62.35; H, 4.55; N, 8.80.

EXAMPLE 41

The compounds 5- and 12-hydroxyeicosatetraenoic acid (5-HETE and 12-HETE) and $LTB_4$ are early arachidonic acid oxidation products in the lipoxygenase cascade, which have been shown to mediate several aspects of inflammatory and allergic response. This is especially true with respect to 5,12-diHETE, which is also denoted as $LTB_4$ [see Ford-Hitchinson, *J. Roy. Soc. Med.*, 74, 831 (1981)]. Compounds which inhibit the $PLA_2$-mediated release of arachidonic acid thereby effectively prevent the oxidation of arachidonic acid to the various leukotriene products via the lipoxygenase cascade. Accordingly, the specificity of action of $PLA_2$ inhibitors can be determined by the activity of test compounds in this assay, which measures the ability of compounds to inhibit the synthesis of $LTB_4$ by rat glycogen-elicited polymorphonuclear leukocytes (PMN) in the presence of exogenous substrate.

The assay is carried out as follows:

Rat polymorphonuclear leukocytes (PMNs) are obtained from female Wistar rats (150-200 g) which receive an injection of 6% glycogen (10 ml i.p.). Rats are sacrificed 18-24 hours post injection by $CO_2$ asphyxiation and the elicited cells are harvested by peritoneal lavage using physiological saline (0.9% NaCl). The exudate is centrifuged at 400 xg for 10 minutes. The supernatant fluid is discarded and the cell pellet is resuspended to a concentration of $2.0 \times 10^7$ cells/mL in HBSS containing $Ca^{++}$ and $Mg^{++}$ and 10 μM L-cysteine.

To 1 mL aliquots of cell suspension, test drugs or vehicle are added, then preincubated at 37° C. for 10 minutes. A23187 (1 μM), [$^3$H]-AA (3.0 μCi/mL) and unlabeled AA (1 μM) are then added and the samples are further incubated for 10 minutes. The reaction is terminated by centrifugation and pelleting cells. Supernatants are then analyzed by HPLC analysis on a 15 cm×4.6 mm ID supelcosil LC-18 (Supelco)(3M) column, using a two solvent system at a flow rate of 1.4 mL total flow as follows:

Solvent A: 70:30 17.4 mM $H_3PO_4$:$CH_3CN$.
Solvent B: $CH_3CN$.
Gradient: (system is equilibrated with Solvent A).

| Time | Percent A | Percent B |
|------|-----------|-----------|
| 0    | 100       | 0         |
| 15.0 | 100       | 0         |
| 20.0 | 65        | 35        |
| 40.0 | 65        | 35        |
| 42.0 | 10        | 90        |
| 50.0 | 10        | 90        |
| 50.1 | 100       | 0         |

Percent solvent changes are accomplished in a linear fashion.

Injections: 140 μL of each supernatant is injected directly onto column and $^3$H arachidonic acid metabolites are monitored using an on-line radioactivity detector (Ramona, Ind./US, Fairfield, N.J.).

Standards: $10^4$-$2.0 \times 10^4$ dpm of eicosanoids of interest are injected in 90 μL EtOH cocktail.

Co-chromatography with standard [$^3$H] leukotriene $B_4$ ($LTB_4$) in medium of stimulated PMN exposed to drug is compared to that found in medium of stimulated cells exposed to no drug, generating percent inhibition.

Results are expressed as percent inhibition at a given compound dose or as an $IC_{50}$ value.

Testing compounds of the invention in this assay gave the following results:

TABLE I

| Compound of Example No. | % Inhibition |
|---|---|
| ketoprofen | −50* (at 10 μM) |
| 1 | 95 (at 0.5 μM) |
| 2 | 91 (at 0.5 μM) |
| 3 | 87 (at 10 μM) |
|   | 38 (at 0.5 μM) |
| 4 | 8 (at 10 μM) |
| 5 | 96 (at 10 μM) |
| 6 | 95 (at 10 μM) |
|   | 81 (at 0.5 μM) |
| 6A | 94 (at 10 μM) |
|   | 63 (at 0.5 μM) |
| 7 | 85 (at 10 μM) |

*a negative value denotes potentiation of cyclooxygenase ($PGE_2$ synthesis)

EXAMPLE 42

The procedure of Example 41 is also employed for the determination of the extent to which compounds of the invention inhibit the synthesis of the arachidonic acid cyclooxygenase oxidation product $PGE_2$.

In this assay, the procedure of Example 41 is carried out as described. However, in order to determine cyclooxygenase activity, the samples are co-chromatographed with authentic reference [$^3$H]-$PGE_2$.

The results are calculated as in Example 41 and presented below:

TABLE II

| Compound of Example No. | % Inhibition |
|---|---|
| ketoprofen | 87 (at 10 μM) |
| 1 | −13* (at 0.5 μM) |
| 2 | −22* (at 0.5 μM) |
| 3 | 8 (at 10 μM) |
|   | −8* (at 0.5 μM) |
| 4 | −31* (at 10 μM) |
| 5 | −275* (at 10 μM) |
| 6 | −191* (at 10 μM) |
|   | −12* (at 0.5 μM) |
| 6A | −79* (at 10 μM) |
|   | −29* (at 0.5 μM) |
| 7 | −268* (at 10 μM) |

*Negative values denote a potentiation of cyclooxygenase ($PGE_2$ synthesis).

EXAMPLE 43

The compounds of the invention are tested in an in vitro isolated phospholipase $A_2$ assay to determine the ability of the test compounds to inhibit the release of arachidonic acid from an arachidonic acid-containing substrate by the action of phospholipase $A_2$ enzyme from human and non-human sources.

This assay is carried out as follows:

Into a 15 mL polypropylene tube are added the following:

| Agent | Volume, μL | Final Conc. |
|---|---|---|
| $^3$H-AA *E. coli* substrate[1] | 25 | 5 nmoles PL |

-continued

| Agent | Volume, μL | Final Conc. |
|---|---|---|
| CaCl$_2$ (0.1 M)[2] | 5 | 5 mM |
| Tris-HCl (0.5 M) pH 7.5[3] | 20 | 100 mM |
| Water[4] | 25 | |
| Drug/vehicle[5] | 1 | 50 μM |
| PLA$_2$ | 25 | Volume yielding 12% hydrolysis in 10 min. |
| | 100 | |

*pre-incubate at room temperature 30 min prior to substrate addition.
[1]Prepared by adding 2 mL deionized and distilled water to 2 mL $^3$H-arachidonate labeled E. coli (lower count), to which is added 1 mL of $^3$H-arachidonate labeled E. coli (higher count) to yield a total of 5 m substrate (containing 1000 nmoles phospholipid).
[2]Stock 0.1 m CaCl$_2$, required for enzyme activity.
[3]Stock 0.5 m Trisma-Base. Stock 0.5 M Trisma-HCl. Adjust pH to 7.5 (optimum for enzyme).
[4]Deionized and distilled water.
[5]Stock 10 mM prepared in dimethyl sulfoxide. Make 1:2 dilution with dimethyl sulfoxide and add 1 μL to 100 μL assay tube.
[6]Two human PLA$_2$ enzymes are used:
a) Semi-purified human platelet acid extract PLA$_2$ (in 10 mM sodium acetate buffer, pH 4.5). Remove protein precipitate by centrifugation at about 2200 rpm to 10 minutes.
b) Purified human synovial fluid.

Incubate the 100 μL reaction mixture for 10 minutes at 37° C. in a shaking water bath. The reaction is terminated by the addition of 2 mL tetrahydrofuran, followed by vortexing. NH$_2$ columns (100 μg/mL- Analytichem International) are conditioned with 0.5 mL tetrahydrofuran followed by 0.5 mL tetrahydrofuran/water (2 mL:0.1 mL, v/v).

The sample is loaded onto the columns and slowly drawn through them. The hydrolyzed arachidonic acid retained in the columns is eluted therefrom with 1 mL tetrahydrofuran/glacial acetic acid (2%). The arachidonic acid is transferred to scintillation vials and quantitated by β-counting analysis. A "total counts" sample is prepared by pipetting 25 μL $^3$H-arachidonate E. coli directly into a scintillation vial to which is added 1 mL tetrahydrofuran. 10 mL aquasol (scintillation cocktail) is added to all samples.

Calculations:

$$\% \text{ hydrolysis} = \frac{[3H]AA \text{ dpm(sample)} - [3H]AA \text{ dpm(nonspecific hydrolysis)}}{\text{total counts dpm}} \times 100$$

$$\% \text{ change} = \frac{\text{vehicle dpm} - \text{drug dpm}}{\text{vehicle dpm}} \times 100$$

Activity of Standard Drugs:

| (μM) | IC$_{50}$ | |
|---|---|---|
| | Human Platelet | Human |
| | Synovial | |
| Drug | PLA$_2$ | PLA$_2$ |
| Arachidonic Acid | 8.6 | 3.2 |
| Monoalide | 25.2 | 0.14 |

When tested in this assay, the compounds of the invention gave the following results:

TABLE III

| Compound of Example No. | % Inhibition at 10 μM HSF* |
|---|---|
| ketoprofen | −16.9** |
| 3 | 25.5 |
| 4 | 15.1 |

*human synovial fluid
**negative values denote a potentiation of HSF

EXAMPLE 44

The compounds of the invention are evaluated for their ability to inhibit the lipoxygenase and/or cyclooxygenase pathways of arachidonic acid metabolism in the in vivo murine zymosan peritonitis assay.

This assay is carried out as follows:

Male CD-1 mice (8 weeks old) are placed in plastic boxes in groups of six. Animals are injected with 1 mL i.p. of either 1% zymosan in pyrogen free 0.9% saline or saline (unstimulated control). Compounds are dosed orally 1 hour prior to zymosan injection. Twenty minutes after zymosan injection, the mice are asphyxiated by CO$_2$ inhalation and the peritoneal cavity is lavaged with 2 mL ice cold Hanks Balanced Salt Solution (HBSS) without CaCl$_2$, MgSO$_4$.7H$_2$O and MgCl$_2$.6H$_2$O. Peritoneal lavage fluid from each mouse is removed by syringe and placed in 5 mL plastic test tubes put on ice and volume is noted. Preparation of samples for evaluation by ELISA is as follows: Samples are centrifuged at 800 xg for 15 minutes; 1 mL of the supernatant is added to 8 mL ice cold methanol and kept at −70° C. overnight to precipitate protein; and samples are then centrifuged at 800 xg for 15 minutes, followed by a drying procedure in a Savant speed vac concentrator. The samples are reconstituted with 1 mL ice cold ELISA buffer and stored at −70° C. until assayed. The assay for eicosanoids (LTC$_4$ and 6-keto-PGF$_{1a}$) is performed according to conventional ELISA procedures.

Compounds to be tested orally are suspended in 0.5% Tween 80. Compounds to be tested intraperitoneally are suspended in 0.5% methylcellulose in 0.9% saline.

The total metabolite level in lavage fluid/mouse is calculated and the significance is determined by a one-way analysis of variance with LSD comparisons to control (p≦0.05). Drug effects are expressed as a percent change from control values.

The activity of standard drugs in this assay is as follows:

| | ED$_{50}$ mg/kg p.o. | |
|---|---|---|
| Compound | LTC$_4$ | 6-keto-PGF$_{1a}$/TxB$_2$ |
| BW755C | <10 | 22.0 |
| Phenidone | 24.0 | <30.0 |
| Indomethacin | Not Active | 0.126 |
| Ibuprofen | Not Active | 7.0 |

When tested in this assay a compound of the invention and the anti-inflammatory compound etodolac gave the following results:

TABLE IV

| Compound of Example No. | Dose mg/kg | % Inhibition | |
|---|---|---|---|
| | | LTC$_4$ | 6-keto-PGF |
| 5 | 10 (i.p.)* | 86 | −27** |

*intraperitoneally administered
**negative values denote potentiation

The results show that the compound of the invention exerts a potent inhibitory effect on the lipoxygenase pathway but not on the cyclooxygenase pathway.

EXAMPLE 45

The compounds of the invention are further tested in the reverse passive Arthus pleurisy assay to evaluate their effectiveness in inflammatory mediator release and/or the fluid and cellular phases of an inflammatory response.

This assay is carried out as follows:

A reverse passive Arthus reaction is induced in the pleural cavity of male Lewis rats (150-200 g; fasted overnight prior to use) by the intravenous administration of bovine serum albumin (BSA; 4 mg/0.2 ml) followed 30 minutes later by the injection of rabbit anti-BSA (1 mg/0.2 ml; lyophilized IgG fraction; Organon Teknika, West Chester, Pa.) into the right pleural space under halothane anesthesia. Drugs or vehicle (0.5% Tween-80) control are administered orally in a volume of 1 ml/100 g body weight at 1 hour prior to the anti-BSA. Animals are sacrificed at either the time of peak eicosanoid production (i.e. 5 minutes after anti-BSA for immunoreactive $TxB_2$ 10 minutes for immunoreactive $LTB_4$, 20 minutes for immunoreactive $LTC_4$) or at the time of peak neutrophil infiltration (4 hours after anti-BSA) by $CO_2$ inhalation. The pleural cavity is then exposed, the fluid exudate removed by gentle vacuum aspiration and the volume of exudate is recorded. For the determination of cellular infiltration, the pleural cavity is rinsed with 3 ml of 0.1% EDTA in sterile saline, and the recovered wash is pooled with the exudate. Cell number is determined on a model ZBI Coulter counter. For determination of eicosanoid production, undiluted pleural exudate is microfuged and the supernatant is extracted with ethanol (8-10 times volume). Extracts are either stored at $-20°$ C., or are evaporated to dryness under a stream of $N_2$ and reconstituted in radioimmunoassay (RIA) buffer.

Eicosanoids are quantitated by RIA according to the procedure specified by the RIA kit manufacturer (Advanced Magnetics, Cambridge, Mass.). Briefly, 100 μl of $^3$H-labeled eicosanoid and 100 μl of specific antibody are sequentially added to 100 μl of extracted pleural exudate in BGG -phosphate buffer which contains 0.01M phosphate, 0.1% bovine gamma globulin and 0.1% sodium azide at pH 7.0. Antibody-bound eicosanoid is separated from unbound eicosanoid by the addition of 750 μl of dextran (0.4%)-coated charcoal (0.4% Norit A) containing 0.1% sodium azide. The mixture is centrifuged at 2000 RPM at 5° C. for 15 minutes to pellet the charcoal and adsorbed unbound eicosanoid. Antibody-bound labeled eicosanoid is quantitated by counting in a liquid scintillation counter, and is correlated to concentration by a standard curve.

Inflammatory cells are expressed as $10^6$ cells/ml, pleural exudate is expressed as ml of fluid, and the amount of eicosanoids in the pleural cavity is expressed as ng/ml of exudate. Mean±S.E.M. is determined for each group. Percent inhibition (% I) of cell number, exudate volume and eicosanoid production is calculated for vehicle-treated control groups, and the responses in drug-treated rats are then expressed as the mean % I of the control. The $ED_{30}$ or $ED_{50}$ with 95% confidence limits is calculated by the method of Litchfield and Wilcoxon, *J. Pharmac. Exp. Ther.*, 96, 99-113 (1949).

The activity of standard drugs in this assay is as follows:

| Antiinflammatory Drug | Class | A. Inflammatory Mediator Release: $ED_{50}$ (mg/kg p.o.) | |
|---|---|---|---|
| | | $TxB_2$ | $LTB_4$ |
| Indomethacin | NSAID; CO inhibitor | 0.16 | 12% Inh (4 mg/kg) |
| Naproxen | | 0.24 | 0% Inh (4 mg/kg) |
| Diclofenac | | 6.0 | 0% Inh (10 mg/kg) |
| Ketoprofen | | 0.18 | 35% Inh (10 mg/kg) |
| Wy-50,259-A | LO Inhibitor | 0% Inh (75 mg/kg) | |
| BW540C | Mixed CO/LO Inhibitor | 19 | 30 |
| BW755C | | 18 | 23 |
| Phenidone | | 69 | 10 |

| Anti-inflammatory Drug | Class | B. Pleural Inflammation: $ED_{30}$ (mg/kg p.o.) | |
|---|---|---|---|
| | | Fluid Exudation | Cellular Influx |
| Indomethacin | NSAID; CO inhibitor | 2.5 | 19% Inh (8 mg/kg) |
| Naproxen | | 3.9 | 29% Inh (8 mg/kg) |
| Piroxicam | | 1.0 | 3.0 |
| BW755C | Mixed CO/LO inhibitor | 14 | 28 |
| Phenidone | | 21 | 23 |
| Dexamethasone | Steroid | 0.05 | 0.13 |

When tested in this assay, the compounds of the invention gave the following results:

TABLE VI

| Compound of Example No. | % Inhibition of $LTB_4$ Synthesis* | $ED_{50}$ (mg/kg) |
|---|---|---|
| 2 | 34 | |
| 9 | | 0.8 |
| 10 | 65 | |
| 15 | 12% at 10 mg/kg | |
| 16 | 46 | |
| 17 | 37 | |
| 18 | 32 | |
| 20 | 19 | |
| 21 | 8 | |
| 22 | 37 | |
| 24 | 56 | |
| 26 | 7 | |
| 30 | 21 | |
| 33 | 2 | |

*At 25 mg/kg p.o. unless otherwise specified, drugs administered 3 hours before challenge.

The results show that the compounds tested have an effect in inhibiting the release of inflammatory mediators and in inhibiting the fluid and cellular phases of the inflammatory response.

EXAMPLE 46

The assay of this Example measures the ability of the compounds tested to inhibit 5-lipoxygenase in human whole blood.

This assay is carried out as follows:

Blood is obtained in 50-100 ml quantities from male donors. White blood cell counts and differentials are made. Two ml of blood are placed in a 15 ml polypropylene test tube. Compounds are solubilized in dimethylsulfoxide and diluted 1:10 in 10% bovine serum albumin in phosphate buffered saline, pH 7.4 resulting in a final dimethylsulfoxide concentration of 0.1% in the blood. Then, compounds are added to the blood in a shaking water bath at 37° C. for 10 minutes prior to the addition of 30 μM calcium ionophore (A23187; Sigma). After ionophore administration, whole blood samples are mixed and incubated for 20 minutes at 37° C. in a shaking water bath. Incubation is terminated by placing samples in an ice bath and immediately adding ethylene glycol-bis-(β-aminoethyl ether)-N,N,N',N'-tetraacetic acid (10 mM). Samples are mixed and centrifuged at 1200×g for 15 minutes at 4° C. Preparation of samples for evaluation by RIA or ELISA is carried out by the following protocol. Plasma is removed from sample tubes, placed in 15 ml polypropylene test tubes containing 8 ml methanol, and then vortexed to precipitate protein. Samples are stored at −70° C. overnight. The next day, samples are centrifuged at 200×g for 15 minutes at 4° C. to pellet the precipitate. Samples are dried in a Savant speed vac concentrator, reconstituted to original volume with ice cold RIA or ELISA buffer, and stored at −70° C. until assayed. The assay for eicosanoids ($LTB_4$, $TxB_2$, and $PGE_2$) is performed as described by the manufacturer of the [$^3$H]-RIA kit or ELISA kit ($LTB_4$-Amersham, $TxB_2$ and $PGE_2$-Caymen Chemical).

The total eicosanoid level in 2 ml of blood is calculated and reported as ng/$10^6$ neutrophils. Significance is determined by a one-way analysis of variance with least significant difference (LSD) comparisons to control (p≦0.05) and $IC_{50}$'s (μM) are determined by regression analysis (Finney, 1978). Drug effects are expressed as percent change from control values.

Compounds tested in vitro are solubilized in dimethylsulfoxide and diluted 1:10 in 10% bovine serum albumin in phosphate buffer saline resulting in a final dimethylsulfoxide concentration of 0.1% in the blood.

The results for compounds of the invention tested in this assay are presented in Table VII.

TABLE VII

| Compound of Example No. | % Inhibition of $LTB_4$* | $IC_{50}$ (μM) |
|---|---|---|
| 2 | 5 | |
| 5 | 11 | |
| 8 | 94 | 0.53 |
| 14 | 5 | |
| 15 | 77 | |
| 16 | 72 | 8.3 |
| 18 | 97 | 0.5 |
| 19 | 83 | |
| 20 | 93 | |
| 21 | 85 | 7.8 |
| 22 | 74 | 9.0 |
| 23 | 32 | 11.9 |
| 26 | 86 | 1.3 |
| 27 | 69 | 1.3 |
| 28 | 66** | 2.3 |
| 29 | 74** | 0.7 |
| 30 | 96** | 0.98 |
| 33 | 10** | |
| 34 | 36** | |
| 35 | 51** | |
| 36 | 77** | |
| 37 | 61** | |
| 38 | 46** | |
| 39 | 43** | |
| 40 | 47** | |

*At 25 μM unless otherwise specified.
**At 10 μM.

EXAMPLE 47

The $LTD_4$ antagonist activity of the compounds of the invention is assessed in the in vitro isolated guinea pig trachea assay.

This assay is carried out as follows:

Male Hartley guinea pigs (350–400 g) are euthanized by a blow to the head, the neck is opened and the trachea removed. The trachea is maintained in aerated physiological salt solution, cleared of connective tissue and fat and cut into rings approximately 2 mm in width (usually containing two cartilaginous segments per ring). Two pieces of silk suture are then passed through the lumen of the tracheal ring and are tied around the cartilage, one on each side of the trachealis muscle. The tracheal ring is suspended between a glass hook and a force displacement transducer in a 10 ml organ bath for measurement of isometric tension. Tissues are maintained at 37° C. in aerated (95% $CO_2$/5% $CO_2$) physiological salt solution of the following composition: NaCl (100 mM), $KH_2PO_4$ (1.18 mM), KCl (4.74 mM), $CaCl_2$ (2.5 mM), $MgSO_4$•$7H_2O$ (1.19 mM), $NaHCO_3$ (25 mM), dextrose (11.1 mM) and indomethacin (1 μM). The tracheal rings are maintained at 2 g resting tension and equilibrated for 45 minutes (with frequent washing and readjustment of resting tension).

The tracheal rings are first contracted by the addition of carbachol ($3\times10^{-6}$M), to determine tissue responsiveness and establish a reference contraction. On attainment of a stable level of contraction (approximately 30 minutes), the tissues are washed several times until baseline tension has been restored and the re-equilibrated for 30 minutes. The tissues are then incubated for 45 minutes with a test antagonist (either $1\times10^{-6}$M or $1\times10^{-5}$M) or 10 μl of an appropriate solvent control (control, non-treated). One tissue in each group serves as the control. Twenty minutes prior to the construction of the $LTD_4$ cumulative concentration-response curve, L-cysteine ($1\times10^{-2}$M final bath concentration) is added to inhibit bioconversion of $LTD_4$ to $LTE_4$. Only one $LTD_4$ concentration-response curve is constructed in each tissue.

All responses to $LTD_4$ in an individual tissue are measured as a percentage of the reference contraction of that tissue to carbachol. $LTD_4$ antagonist activity is determined by comparison of the concentration response curves of $LTD_4$ in the presence and absence of antagonist. Assessment of the relative rightward shift of the antagonist treated curve relative to the solvent (control) treated tissue is calculated as a concentration ratio (Eq. A) and used in subsequent calculations to derive an antagonist $pK_B$ value (Eqs. B and C). In the event that the maximum response to $LTD_4$ is depressed, the $EC_{50}$ for that particular curve is determined, an "apparent" $pK_B$ reported, and the compound reported as "not-competitive."

$$\text{Concentration Ratio } (CR) = \frac{EC_{50} \text{ treated tissue}}{EC_{50} \text{ control}} \quad \text{A)}$$

$$K_B = \frac{[\text{Test Compound}]}{CR - 1} \quad \text{B)}$$

$$-\log K_B = pK_B \quad \text{C)}$$

If a compound is found to be active and/or depress the maximal response to $LTD_4$, then a range of concentrations of the test compound should be used generating multiple concentration ratios which would then be used to perform a Schild analysis, and determination of a pA$_2$ value where appropriate.

The activity of reference leukotriene antagonists in this assay is as follows:

| Compound | pK$_B$ |
|---|---|
| Ly-171,883 | 7.44 ± 0.12 |
| Wy-48,252 | 6.90 ± 0.23 |

When tested in this assay, a compound of the invention gave the following results:

TABLE VIII

| Compound of Example No. | pK$_B$ | Concentration Ratio (M) |
|---|---|---|
| 2 | 6.2 | 1 × 10$^{-5}$ |
| 5 | 6.5 | 1 × 10$^{-5}$ |
| 14 | <5.1 | 1 × 10$^{-5}$ |
| 15 | <5.0 | 1 × 10$^{-5}$ |
| 17 | <5.5 | 1 × 10$^{-5}$ |
| 18 | <5.1 | 1 × 10$^{-5}$ |
| 20 | <5.2 | 1 × 10$^{-5}$ |
| 21 | <5.0 | 1 × 10$^{-5}$ |
| 22 | 5.3 | 1 × 10$^{-5}$ |
| 24 | 6.0 | 1 × 10$^{-5}$ |
| 25 | <5.1 | 1 × 10$^{-5}$ |
| 26 | <5.0 | 1 × 10$^{-5}$ |
| 28 | <5.4 | 1 × 10$^{-5}$ |
| 29 | 6.2 | 1 × 10$^{-5}$ |
| 33 | <5.0 | 1 × 10$^{-5}$ |
| 34 | <5.0 | 1 × 10$^{-5}$ |
| 35 | <5.3 | 1 × 10$^{-5}$ |
| 37 | <5.5 | 1 × 10$^{-5}$ |

The above results demonstrate that the compounds tested exhibit leukotriene antagonist activity as measured in the in vitro isolated guinea pig trachea assay.

EXAMPLE 48

The ability of the compounds of the invention to inhibit the biosynthesis of LTB$_4$ by isolated human neutrophils is evaluated in the following assay, which is carried out in this manner:

Isolation of Human Polymorphonuclear Neutrophils

A leukocyte enriched blood sample obtained from a healthy male donor is procured by leukophoresis using a Haemonetics model 30+ blood processor (Biological Specialties, Inc., Lansdale, Pa.). The top "platelet-rich" layer is removed after a low speed spin (35×g, 15 min, 25° C.) of the sample. The remaining cell suspension is centrifuged (400×g, 10 min, 25° C.) to sediment the remaining cells. The supernatant is discarded and the cell pellet resuspended in 120 ml HBSS (without Ca$^{++}$/Mg$^{++}$). The cell suspension is subjected to ficoll-hypaque sedimentation (Histopaque 1077, 400×g, 30 min, 25° C.). Contaminating erythrocytes are lysed by hypotonic shock (1 min). The cells are then washed once with 40 ml of HBSS and resuspended with HBSS (without Ca$^{++}$/Mg$^{++}$) to a concentration of 2.5×10$^7$ cells/ml for further use. Greater than 95% purity is obtained as assessed by microscopic examination.

LTB$_4$ Biosynthesis in Human PMN

One ml of human PMN (2.5×10$^7$ cells/ml) is incubated with vehicle or drugs (10 μl) for 10 min at 30° C. After preincubation, an equal volume of HBSS (1 ml) containing 2.4 mM CaCl$_2$, 6 μM calcium ionophore A23187 and 50 μCi [$^3$H]-acetate is then incubated at 30° C. for 15 minutes. An aliquot (100 μl) of the reaction mixture is taken out and mixed with 900 μl of 15% ethanol. LTB$_4$ is extracted by using solid phase extraction on reverse phase C$_{18}$ columns to remove excess [$^3$H]-acetate and PAF. The C$_{18}$ column is prewashed once with 2 ml of ethanol and water. The sample aliquot is acidified with 0.1N HCl to pH3 before applying to the column. The column is then washed with 2 ml of water followed by 2 ml of 15% ethanol and 2 ml of petroleum ether to remove excess labeled acetate. The sample is eluted with 2 ml of ethyl acetate. The collected samples are dried with nitrogen and resuspended in 0.5 ml RIA buffer. The quantity of LTB$_4$ in the sample is obtained from RIA determination.

Data presented are the means +/− s.d. of the values relative to control A23187 stimulated cells for each experiment assayed in triplicate. Percent inhibition when used is calculated as:

% Inhibition = 100 − [(x ÷ Control) × 100]

Dose response analysis is performed by non-linear regression analysis for curve fitting and IC$_{50}$ determination.

The results for compounds of the invention tested in this assay are presented in Table IX.

TABLE IX

| Compound of Example No. | % Inhibition of LTB$_4$ Synthesis* |
|---|---|
| 12 | Inactive |
| 13 | 98.9 |
| 21 | 91.2 |
| 23 | 99.0 |
| A-64,077 | 75.8 |

*At 2.5 μM.

What is claimed is:
1. A compound having the formula

A(CH$_2$)$_n$O—B wherein
A is a group having the formula wherein
X is —N—;
Z is —S— or —O—;
R$^1$ is hydrogen, lower alkyl or phenyl;
R$^2$ is hydrogen or lower alkyl; or
R$^1$ and R$^2$ taken together form a benzene ring,
with the proviso that when B is a substituted diphenyloxazole, A is also phenyl, unsubstituted or mono or adjacent dilower alkyl substituted, or naphthyl;
n is 1-2;
B is -continued

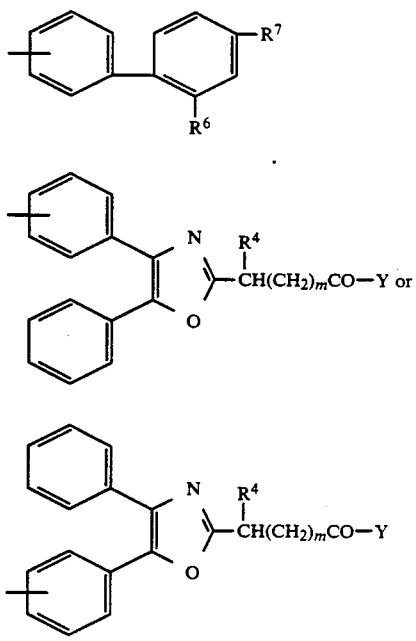

wherein
Y is $OR^5$ or $N(OH)R^8$;
$R^4$ and $R^5$ are each, independently, hydrogen or lower alkyl;
$R^6$ is hydrogen, halo or nitro;
$R^7$ is

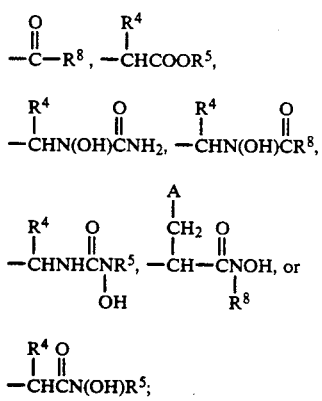

$R^8$ is lower alkyl;
m is 0–3;
and the pharmacologically acceptable salts thereof.

2. The compound of claim 1, having the name 4-[4-[2-naphthalenyl-methoxy]phenyl]-5-phenyl-2-oxazole propanoic acid.

3. The compound of claim 1, having the name 4-[4-[2-naphthalenyl-methoxy]phenyl]-5-phenyl-2-oxazole propanoic acid methylester.

4. The compound of claim 1, having the name 4-[4-[(1-methyl-1H-benzimidazol-2-yl)methoxy]phenyl]-5-phenyl-2-oxazole propanoic acid.

5. The compound of claim 1, having the name 4'-(2benzothiazolylmethoxy)-4-diphenylacetic acid, ethyl ester.

6. The compound of claim 1, having the name 4'-(benzothiazolylmethoxyl)-4-diphenylacetic acid.

7. The compound of claim 1, having the name 4'-(benzothiazolylmethoxy)-4-diphenyl-N-hydroxy-N-methyl-acetamide.

8. The compound of claim 1, having the name N-hydroxy-4'-(2-benzothiazolylmethoxy)-[1,1'-biphenyl]-4-acetamide.

9. The compound of claim 1, having the name N-hydroxy-N-isopropyl-4'-(2-benzothiazolylmethoxy)-[1,1'-biphenyl]-4-acetamide.

10. The compound of claim 1, having the name N-hydroxy-N,α-dimethyl-4'(2-benzothiazolylmethoxy)-[1,1'-biphenyl]-4-acetamide.

11. The compound of claim 1, having the name N-hydroxy-N,α-dimethyl-4'-(2-benzothiazolylmethoxy)-[1,1'-biphenyl]-4-acetamide.

12. The compound of claim 1, having the name N-hydroxy-N-methyl-4'-[(2-phenylthiazol-4yl)methoxy]-[1,1'-biphenyl]-4-acetamide.

13. The compound of claim 1, having the name N-hydroxy-N-methyl-4'-[(2-phenylthiazol-4-yl)methoxy]-[1,1'-biphenyl]-4-acetamide.

14. The compound of claim 1, having the name N-hydroxy-N-isopropyl-4'-[(2-phenylthiazol-4-yl)methoxy]-[1,1'-biphenyl]-4-acetamide.

15. The compound of claim 1, having the name N-hydroxy-N,α-dimethyl-4'-[(2-phenylthiazol-4-yl)methoxy]-[1,1'-biphenyl]-4-acetamide.

16. The compound of claim 1, having the name N-hydroxy-N,α-dimethyl-4'-[(2-phenylthiazol-4-yl)methoxy]-[1,1'-biphenyl]-4-acetamide.

17. The compound of claim 1, having the name N-hydroxy-N-methyl-2-phenyl-α-[4'-[(2-phenylthiazol-4-yl)methoxy]-[1,1'-biphenyl]-4-yl]-thiazolepropanamide.

18. The compound of claim 1, having the name 4'-(benzothiazolylmethoxy)-2-fluoro-N-hydroxy-N-methyl-[1,1'-biphenyl]-4-acetamide.

19. The compound of claim 1, having the name 2-fluoro-N-hydroxy-N-methyl-4'-[2-phenyl-4-thiazolyl)-methoxy]-[1,1'-bipheynl]-4-acetamide.

20. The compound of claim 1, having the name 2-{3-[4-(benzothiazol-2-ylmethoxy)-benzoyl]-phenyl}-N-hydroxy-N-methyl-4-acetamide.

21. The compound of claim 1, having the name 4-{4-[(1-methyl-1H-benzimidazol-2-yl)methoxy]phenyl}-5-phenyl-2-oxazole N-hydroxy-N-methyl propanamide.

22. The compound of claim 1, having the name 4-{4-[(benzothiazol-2-yl)methoxy]-phenyl}-5-phenyl-2-oxazole N-hydroxy-N-methyl propanamide.

23. The compound of claim 1, having the name 1-{1-[4'-(benzothiazol-2-ylmethoxy)biphenyl-4-yl]-ethyl}-1-hydroxy-urea.

24. The compound of claim 1, having the name N-{1-[4'-(benzothiazol-2-ylmethoxy)-biphenyl-4-yl]-ethyl}-N-hydroxy-acetamide.

25. The compound of claim 1, having the name 1-{1-[4'-(benzoxazol-2-ylmethoxy)-biphenyl-4-yl]-ethyl}-1-hydroxy-urea.

26. The compound of claim 1, having the name N-{1-[4'-(benzoxazol-2-ylmethoxy)-biphenyl-4-yl]ethyl}-N-hydroxy-acetamide.

27. The compound of claim 1, having the name 1-{1-[4'-(2-phenylthiazol-4-ylmethoxy)-biphenyl-4-yl]-ethyl}-1-hydroxy-urea.

28. The compound of claim 1, having the name N-{1-[4'-(2-phenylthiazol-4-ylmethoxy)-biphenyl-4-yl]-ethyl}-N-hydroxy-acetamide.

29. The compound of claim 1, having the name 1-{1-[4'-(benzothiazol-2-ylmethoxy)-2-fluoro-(1,1'-biphenyl)-4-yl]-ethyl}-1-hydroxy-urea.

* * * * *